United States Patent
de Luis et al.

(10) Patent No.: US 7,838,716 B2
(45) Date of Patent: Nov. 23, 2010

(54) HIGH SPEED SWELLING, PRESSURE EXERTING HEMOSTATIC DEVICE

(75) Inventors: Javier de Luis, Cambridge, MA (US); Marco Serra, Lucca (IT); Timothy Sutherland, Cambridge, MA (US); Liping Sun, North Andover, MA (US)

(73) Assignee: FEG Holdings, LLC, Strongsville, OH (US)

( * ) Notice: Subject to any disclaimer, the term of this patent is extended or adjusted under 35 U.S.C. 154(b) by 7 days.

(21) Appl. No.: 11/891,660

(22) Filed: Aug. 10, 2007

(65) Prior Publication Data

US 2008/0071207 A1   Mar. 20, 2008

Related U.S. Application Data

(60) Provisional application No. 60/837,399, filed on Aug. 11, 2006.

(51) Int. Cl.
  *A61F 13/00*   (2006.01)
  *A61L 15/16*   (2006.01)
  *A61L 15/00*   (2006.01)

(52) U.S. Cl. .................... 602/46; 602/56; 424/445; 424/447

(58) Field of Classification Search .............. 602/56, 602/46, 48, 41, 42; 424/443–449, 78.05, 424/78.06, 78.07; 604/381, 381.01
See application file for complete search history.

(56) References Cited

U.S. PATENT DOCUMENTS

| | | | | |
|---|---|---|---|---|
| 4,293,609 A | * | 10/1981 | Erickson | 428/201 |
| 4,541,426 A | * | 9/1985 | Webster | 602/47 |
| 4,957,795 A | * | 9/1990 | Riedel | 428/74 |
| 5,203,350 A | * | 4/1993 | Duncan et al. | 128/849 |
| 5,759,570 A | * | 6/1998 | Arnold | 424/443 |

(Continued)

FOREIGN PATENT DOCUMENTS

EP   1318778   6/2003

(Continued)

OTHER PUBLICATIONS

Castaneda, F. et al., "Gelatin Sponge Closure Device Versus Manual Compression After Peripheral Arterial Catheterization Procedures," *J. Vasc. Interv. Radiol.*, vol. 14, No. 12, Dec. 2003.

(Continued)

*Primary Examiner*—Patricia M Bianco
*Assistant Examiner*—Ophelia Hawthorne
(74) *Attorney, Agent, or Firm*—Wolf, Greenfield & Sacks, P.C.

(57) ABSTRACT

The present invention provides devices and methods for treating wounds. The devices may include polymer particles capable of absorbing fluid such as blood. When devices of the invention are exposed to fluid, the fluid may enter the device and cause the polymer particles to swell. Devices of the invention may also apply pressure on wound cavities to stop or restrict the flow of fluid. In some embodiments, the devices may comprise components to facilitate absorption of fluid throughout the device, such as wicking elements and/or multiple compartments. One or more of the devices can be placed directly in the wound cavity, or in a containment structure and then into the wound cavity.

76 Claims, 13 Drawing Sheets

U.S. PATENT DOCUMENTS

| | | | |
|---|---|---|---|
| 5,792,471 A * | 8/1998 | Curatolo | 424/480 |
| 5,824,004 A * | 10/1998 | Osborn et al. | 604/385.04 |
| 5,981,822 A * | 11/1999 | Addison | 602/41 |
| 5,998,032 A * | 12/1999 | Hansen et al. | 428/403 |
| 6,599,523 B2 | 7/2003 | Cohen et al. | |
| 6,627,785 B1 | 9/2003 | Edwards et al. | |
| 6,660,301 B1 * | 12/2003 | Vogel et al. | 424/489 |
| 6,911,437 B2 | 6/2005 | Edwards et al. | |
| 7,534,235 B2 * | 5/2009 | Mizutani et al. | 604/385.17 |
| 2004/0005350 A1 * | 1/2004 | Looney et al. | 424/445 |
| 2004/0013715 A1 * | 1/2004 | Wnek et al. | 424/445 |
| 2006/0015053 A1 * | 1/2006 | Crisp | 602/43 |
| 2007/0009586 A1 | 1/2007 | Cohen et al. | |
| 2007/0021703 A1 * | 1/2007 | McCarthy | 602/43 |

FOREIGN PATENT DOCUMENTS

| | | |
|---|---|---|
| WO | WO 02/22059 | 3/2002 |
| WO | WO 2006/0088912 A2 | 8/2006 |

OTHER PUBLICATIONS

Koreny, M. et al., "Arterial Puncture Closing Devices Compared With Standard Manual Compression After Cardiac Catheterization," *JAMA*, vol. 291, No. 3, Jan. 2004.

International Search Report and Written Opinion from International Application No. PCT/US2007/017753, issued on May 20, 2008.

* cited by examiner

HIGH SPEED SWELLING, PRESSURE EXERTING HEMOSTATIC DEVICE

RELATED APPLICATIONS

This application claims the benefit under Title 35, U.S.C. §119(e) of co-pending U.S. provisional application Ser. No. 60/837,399, filed, Aug. 11, 2006, which is incorporated herein by reference.

STATEMENT REGARDING FEDERALLY SPONSORED RESEARCH

This invention was made with U.S. Government support under contract number W81XWH-05-C-0044, monitored by U.S. Army Institute of Surgical Research. The Government has certain rights in the invention.

FIELD OF INVENTION

The present invention relates to devices and methods for the treatment of injuries which produce bleeding, including high volume, high pressure bleeding in proximal extremities.

BACKGROUND OF THE INVENTION

It is known that up to 10% of battlefield fatalities occur because soldiers bleed to death due to wounds inflicted on their proximal extremities, where it is often not possible to apply standard first aid methods, such as a tourniquet. For example, often, the only way to treat injuries to the femoral artery is to locate the artery and clamp it. In battlefield conditions, performing such work is not always possible, nor is it simple to do. Soldiers often operate in environments where it is cold, wet, and dark, making the medic's job that much more difficult. An injury to a major artery must be treated quickly to prevent life-threatening hemorrhage.

The average sized adult male's blood volume is approximately 6 liters. The loss of about 20% of this blood volume, without fluid replenishment to ensure blood pressure is maintained, is potentially fatal. With fluid replenishment it is possible for a person in good health to lose up to 50% of the blood volume without a transfusion and still survive, as long as the total circulation fluid volume remains around 6 liters. However, this type of intervention is often not possible in the field.

Many of these deaths could be prevented through the development of devices and techniques suitable for application in the field as temporary measures for immediate treatment. This is a problem that has, and continues to, receive much attention. Castaneda et al. (Castaneda, F., Swischuk, J. L., Smouse, H. B., Brady, T., "Gelatin Sponge Closure Device Versus Manual Compression After Peripheral Arterial Catheterization Procedures," *J. Vasc. Interv. Radiol.*, Vol. 14, No. 12, December 2003) evaluated the safety and efficacy of a porcine gelatin sponge intended to be used as an alternative to manual compression after a single interventional radiology practice. Their "QuickSeal" system delivers the extravascular sponge over a wire. Although this system appeared to provide benefit, it is unlikely that such an approach would be of use on the battlefield because it requires an operating theater environment and a small, clean wound.

Another study into the effectiveness of Arterial Puncture Closing Devices (APCD's) conducted by Koreny et al. (Koreny, M., Riedmuller, E., Nikfardjam, M., Siostrzonek, P., Mullner, M, "Arterial Puncture Closing Devices Compared With Standard Manual Compression After Cardiac Catheterization," *JAMA*, Vol. 291, No. 3, January 2004) showed that many of the devices intended to accelerate the healing process after procedures such as coronary angiography and percutaneous vascular interventions are not very effective, and in some cases have negative effects. The study concluded that the APCD's analyzed showed only marginal evidence that they are effective and there is reason for concern that they may actually increase the risk of hematoma and pseudoaneurysm.

U.S. Patent Publication No. 2004/0013715 discloses an example of a hemostatic device containing a swellable polymer. However, the device described by the this patent publication does not appear to be ideally suited to preventing the clotting and gelling of blood from inhibiting absorption of blood by the polymer and preventing maximal swelling of the device.

While these and other conventional hemostatic materials and methods for controlling bleeding are potentially useful in certain situations and under certain conditions, a need exists for improved hemostatic devices and methods for their use.

SUMMARY OF THE INVENTION

The present invention relates to hemostatic devices for treating a wound, comprising at least one porous membrane forming at least one enclosure having an interior and an exterior; a plurality of absorbent polymer particles contained in the interior of the enclosure, the polymer particles collectively forming a polymeric mass and being configured to swell in the presence of a fluid; and a plurality of wicking elements contained in enclosure, the wicking elements capable of transporting fluid into an interior region of the polymeric mass.

The present invention also relates to hemostatic devices for treating a wound, comprising, at least one porous membrane defining at least one enclosure having an interior and an exterior, and a plurality of hemostatic units contained in the interior of the at least one enclosure, wherein each hemostatic unit contains a plurality of polymer particles collectively forming a polymeric mass configured to swell in the presence of a fluid.

The present invention also provides methods for treating a wound, comprising forming a hemostatic device containing a plurality of polymer particles within at least one enclosure formed by one or more porous membranes, the polymer particles collectively forming a polymeric mass and configured to swell in the presence of a fluid the hemostatic device further containing a plurality of wicking elements contained in the enclosure, the wicking elements capable of transporting fluid into an interior region of the polymeric mass; and inserting the hemostatic device into a wound cavity.

The present invention also provides methods for treating a wound, comprising inserting any inventive device described herein into a wound cavity.

BRIEF DESCRIPTION OF THE DRAWINGS

The accompanying drawings are schematic and are not intended to be drawn to scale. In the figures, each identical, or substantially similar component that is illustrated in various figures is typically represented by a single numeral or notation. For purposes of clarity, not every component is labeled in every figure, nor is every component of each embodiment of the invention shown where illustration is not necessary to allow those of ordinary skill in the art to understand the invention. In the drawings.

DETAILED DESCRIPTION OF THE INVENTION

Figure 1:
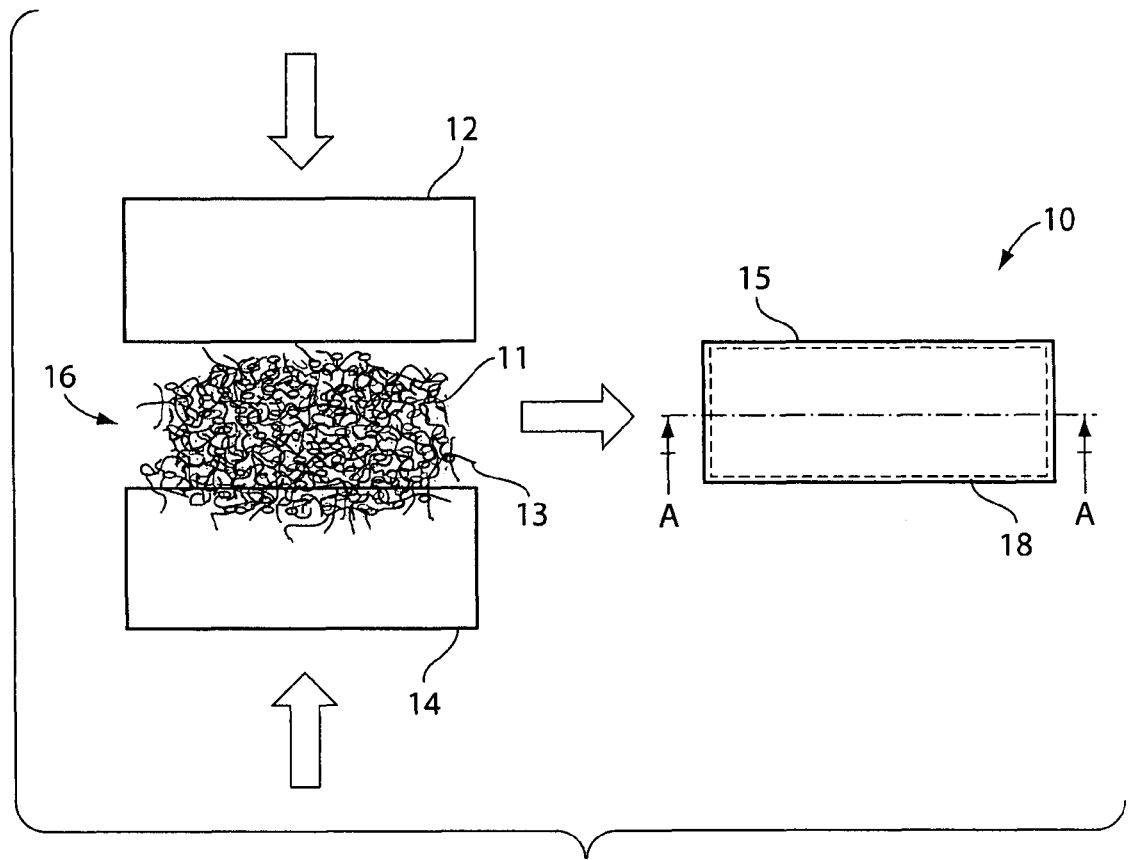
FIG. 1 shows a hemostatic device and a method of its assembly, according to one embodiment of the invention.

Generally disclosed herein are hemostatic devices and methods for absorption of fluids (e.g., blood) using the devices. In some cases, the hemostatic devices of the invention utilize superabsorbent polymers to absorb fluids, causing the devices to swell. The devices, when swollen, can be used to exert pressure on the walls of a cavity to substantially reduce or stop the flow of fluid into and from the cavity. In certain embodiments, the present invention provides hemostatic devices that, when placed in or on a wound, are capable of exerting sufficient pressure on the interior surface of the wound cavity in order to stop, or substantially reduce, the loss of blood. In some cases, the devices may also facilitate clotting of blood by, for example, absorbing fluid.

The hemostatic devices and methods of certain embodiments may be particularly advantageous for treatment of battle-inflicted and traumatic wounds in which there is substantial damage and the wound cavity is substantially irregular in shape. Devices and methods of certain embodiments of the invention can provide the opportunity to treat wounds in the proximal extremities and torso, where a tourniquet cannot be used. Certain embodiments of the present invention may also be used to serve as a critical emergency first aid device to extend the time available for treatment of a wound to enable enough time for transport of the victim to a suitable facility for treatment. Certain embodiments of the inventive devices are able to conform to any wound shape and may be adjustable in size.

In some embodiments, devices of the invention advantageously have the ability to exert controlled pressure to and/or in a wound independently, i.e., without manual compression, making embodiments of the invention useful in the treatment of certain non-compressible wounds, such as non-compressible abdominal wounds. Another advantage of certain devices of the invention is the ability to enhance coagulation or clotting of blood. In some embodiments, devices of the invention may also be useful in the treatment of traumatic pelvic injuries. In an illustrative embodiment, a device of the invention may be introduced through a retroperitoneal approach in the pelvis via a suprapubic incision. It is possible that the hemostat may represent a better alternative than laparotomy pads for effective packing in such embodiments.

One basic function of devices of certain embodiments of the present invention is to serve as a blood absorption and/or pressure exertion device (e.g., a plug) in wounds that exhibit high-pressure bleeding, such as wounds that may be inflicted on the battlefield by flying shrapnel or gunshots, and in traumatic accidents of any kind. These wounds may be highly irregular and present treatment problems if they are suffered in the proximal extremities. For example, a particular area of interest for certain embodiments of this invention relates to groin injuries, which often cannot be treated with a tourniquet and, as a result, cause a high percentage of deaths by exsanguination. Devices and methods of certain embodiments of the invention can enable the quick treatment of severe bleeding by the application of pressure directly on the walls of the wound cavity and on damaged blood vessels by certain devices of the invention. The pressure applied may be sufficient to balance that which drives the blood flow in conditions of severe bleeding. Whilst under pressure, devices of certain embodiments of the invention can form a seal within the wound cavity, impeding the flow of blood through the cavity and effectively plugging the wound. In other embodiments, agents that promote blood clotting, as well as any other medicinal agents, may be included. Such devices can have the added advantage of exerting pressure only where needed without cutting blood flow to the surrounding areas.

Figure 3:
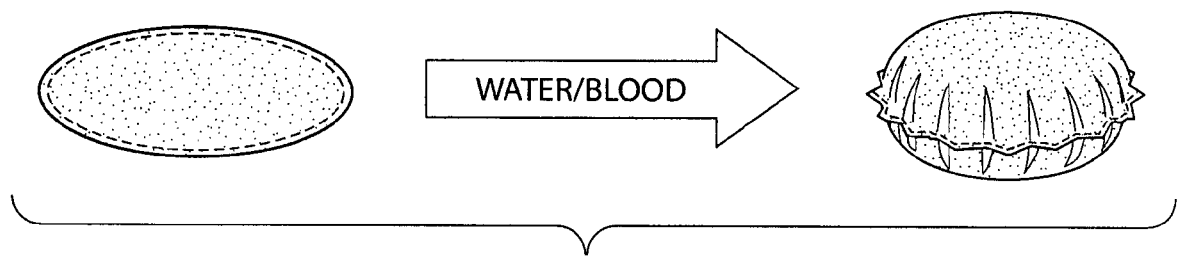
FIG. 3 shows one embodiment of a hemostatic device which swells upon absorption of a fluid.

In some embodiments, devices of the invention comprise a plurality of superabsorbent polymer particles contained within an enclosure, such as a membrane, for example, which may be elastic or inelastic. Fluid, in such embodiments, can pass through the membrane and contact the polymer particles, which swell upon absorption of the fluid, causing the device to undergo geometric changes and to increase in size. FIG. 3 shows an illustrative embodiment, wherein the device, in the absence of fluid, may be substantially flat, and, in the presence of fluid, may adopt a swollen, inflated shape upon absorption of the fluid. As a result of this swelling, the hemostatic device becomes swollen and thereby can be used to apply pressure to a wound cavity.

One advantageous feature of certain embodiments of the present invention relates to the ability to achieve enhanced swelling of superabsorbent polymer particles within the hemostatic device, enabling the device to rapidly produce an enhanced amount of pressure on or within a wound. In some cases, devices which employ swelling action of superabsorbent polymers to absorb, for example, blood, may experience premature gelling of the blood at the surface of the device due to the coagulation properties of blood around a foreign object. The swelling behavior of superabsorbent polymers may be dramatically different in, for example, water, than it is in blood due to the particulate content and coagulation properties of blood, which can give rise to different swelling kinetics. For example, in water, regardless of the salinity which affects ultimate swollen volume, a polymeric mass comprising a plurality of superabsorbent polymer particles contained in a bag may swell freely since the flow paths do not become obstructed until sufficient pressure is built up to compress the polymer particles onto each other. In blood, however, the polymer particles have a tendency to swell quickly on the outer surface of the polymeric mass, but the coagulation and particulate content of the blood may agglomerate in the flow channels between particles and can cause the outer layer to gel and block the further ingress of blood, leaving the interior of the polymeric mass dry and unswollen. That is, clotted or coagulated blood may form a layer on the outer surface of the device and prevent further absorption of blood, such that a portion of the superabsorbent polymer material located in interior portions of the device is prevented from contacting the blood and, thus, does not swell. In some cases, a sufficiently large portion of the superabsorbent polymer material is prevented from swelling such that the ability of the device to exert adequate pressure on the wound is hampered.

Without being bound by any particular theory or mechanism of action, it is believed that certain embodiments of the hemostatic devices of the present invention cause rapid absorption of aqueous component(s) of the blood during swelling, resulting in dehydration of the blood. This, in some embodiments, can facilitate, accelerate, or otherwise enhance clotting. The rate of this process may be modulated, for example, to reduce or prevent premature clotting that may prevent optimal swelling.

Accordingly, some embodiments of the invention make use of wicking elements, to promote the transport of fluid (e.g., blood fluids) into interior portions of a hemostatic device to achieve enhanced swelling of the device. In some certain embodiments, wicking elements are used to facilitate the exertion of pressure in/on a wound as well as for enhancing the clotting of blood. A "wicking element," as used herein, is given its ordinary meaning in the art and refers to a hydrophilic material having the ability to transport fluid via capillary action. The wicking elements may be in the form of fibers (or yarn/thread comprising multiple fibers), beads, tubes, sheets, or the like. In one embodiment, the wicking elements transport fluid from an outer surface of a polymeric mass formed of absorbent polymer particles within the hemostat, which outer surface is in direct contact with the fluid, to an inner portion not in direct contact, or not initially in direct contact, with the fluid. Examples of suitable hydrophilic materials for forming the wicking elements include, but are not limited to, polyester, nylon, acrylic, cellulosic, or other not naturally hydrophilic materials that have been rendered hydrophilic, for example, via a surface coating. Inclusion of wicking elements in hemostatic devices described herein may increase the rate and amount of fluid absorbed by devices of the invention and the degree of swelling by increasing the exposure of superabsorbent polymer particles to fluid.

As described more fully below, hemostatic devices of the invention may be constructed and arranged in various configurations. In some embodiments, one or more hemostatic devices may be inserted into the wound cavity individually and/or grouped together as a multi hemostatic unit device. For example, in certain embodiments, a plurality of hemostatic units, each comprising a small hemostatic device, may be enclosed in a containment structure such as a membrane, bag, or other enclosure to form a larger hemostatic device. In other embodiments, a plurality of hemostatic units comprising isolated polymeric masses of absorbent polymeric particles, may be enclosed by one or more membranes such that they comprise separate compartments within a multi-compartment hemostatic device. Similar to the use of wicking elements, partitioning the overall mass of absorbent polymer material in the hemostatic device into a plurality of discrete, smaller hemostatic units, can serve to reduce premature coagulation and blood solids from preventing blood fluids from being able to gain access to all of the absorbent polymer material of the device. In certain embodiments, the use of wicking elements may be combined with a multi-hemostatic unit construction of the hemostatic device to even further enhance the degree of fluid uptake and swelling achieved by the device in use.

In certain embodiments, the present invention provides a hemostatic device for treating a wound, wherein the device comprises an enclosure comprising a porous membrane having an interior and an exterior, and at least one, and more typically a plurality, of polymer particles contained in the interior of the enclosure. In certain embodiments, the polymer particles and any optional wicking elements associate together to collectively form a polymeric mass and are configured to swell in the presence of a fluid, such as blood. The hemostatic device may further comprise a plurality of wicking elements (e.g., wicking fibers, wicking beads, etc.) contained in the interior of the membrane enclosure, wherein the wicking elements are capable of transporting fluid into an interior region of the polymeric mass. In one embodiment, the device is constructed by blending and optionally bonding (e.g. with a polymer such as propylene glycol as described in more detail below) a plurality of polymer particles (e.g., superabsorbent polymer particles) with a plurality of wicking fibers and inserting the material into a porous membrane enclosure, such as a porous bag constructed from, for example, a honeycomb Lycra knit. The device may be designed to absorb blood from high volume, high pressure bleeding wounds and to swell and exert pressure directly on the bleeding site. The device may also form a mechanical seal at the site, for example, if the swollen polymer particles fill in any empty space between the particles, to effectively seal the flow of blood.

In some cases, the hemostatic device is specifically designed for large, traumatic wounds. In some cases, the device is designed to address other types of bleeding wounds. In some embodiments, the device may be inserted directly into a wound cavity. In other embodiments, the device may be arranged within in a bandage placed onto or over a wound.

Figure 1A:
FIG. 1A shows a cross-sectional view of the hemostatic device of FIG. 1.

FIGS. 1 and 1A show an illustrative embodiment of a hemostatic device. Hemostatic device 10 comprises a first membrane 12, a second membrane 14, and absorbent material 16 contained between the membranes 12 and 14. Material 16 may comprise a blend of superabsorbent polymer particles 11 and wicking elements, such as wicking fibers 13, and may further include other fibrous fillers. As described herein, the wicking material may reduce coagulation of blood on the outer surface 15 of the device, which can reduce premature gelling and promote transport of fluid (e.g., blood fluids) past the outer surface 15 of hemostatic device 10 and into absorbent material 16. Membranes 12 and 14 may be joined along their outer edges to form a seal 18 by gluing, sewing, heat sealing, or any other suitable sealing method known to those skilled in the art.

Figure 2:
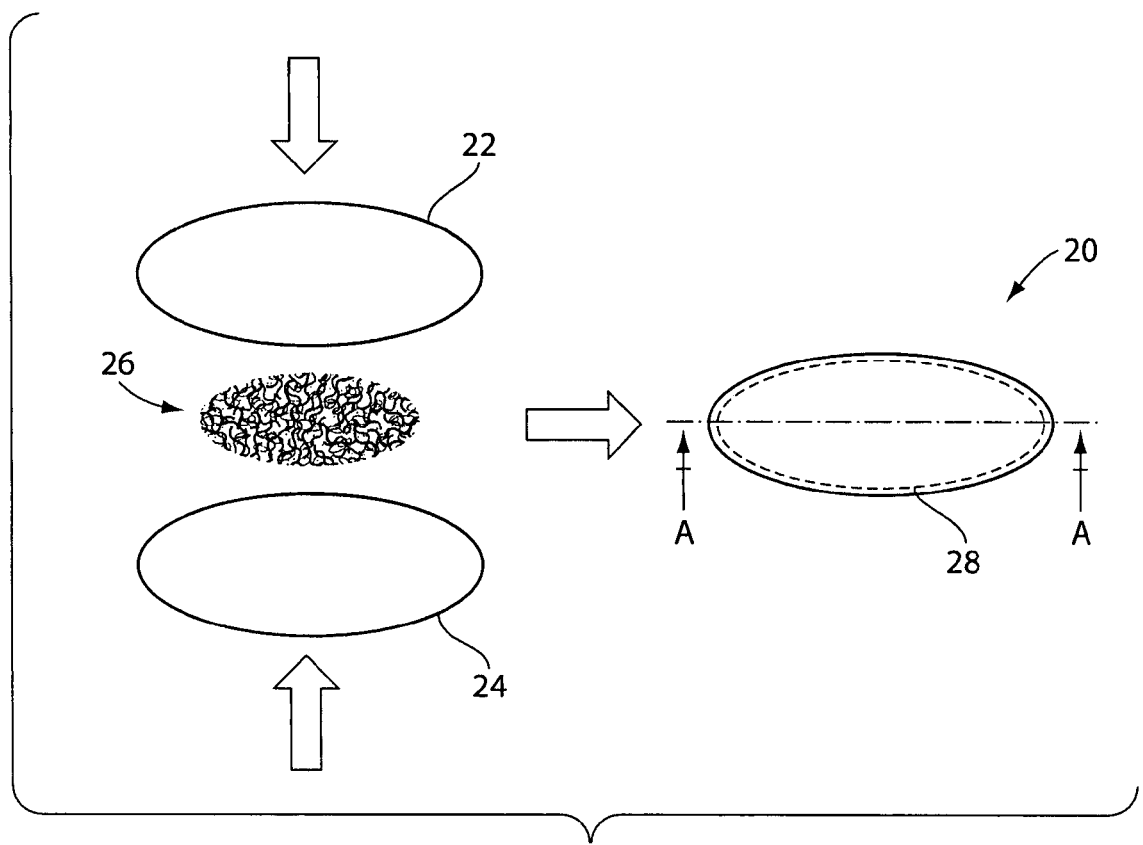
FIG. 2 shows a hemostatic device and a method of its assembly, according to another embodiment of the invention.
Figure 2A:
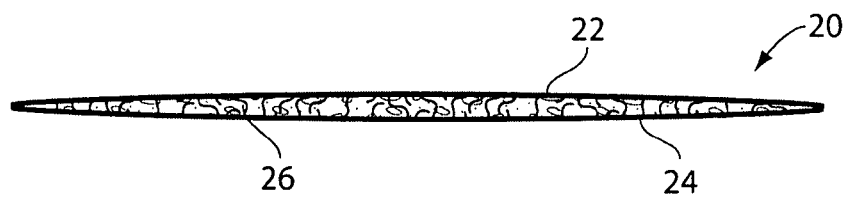
FIG. 2A shows a cross-sectional view of the hemostatic device of FIG. 2.

FIGS. 2 and 2A illustrate another embodiment of the invention, wherein hemostatic device 20 is shaped like a disc and comprises a first membrane 22 and a second membrane 24 joined along their outer edges, while encapsulating a material 26 between membranes 22 and 24. Material 26 may comprise a blend of superabsorbent polymer particles and wicking fibers, as described above. Membranes 22 and 24 can be joined as described above to form seal 28. It should be understood that devices of the invention can be made in a variety of shapes, sizes, and configurations suitable for a particular application. In some cases, the device may have dimensions (e.g., length, width) in the range of about 5 mm to about 200 mm, with a typical range of about 20 mm to 100 mm. The device thickness may range from about 1 mm to about 50 mm, with a typical range being 5 mm to about 20 mm.

A single hemostatic device or multiple hemostatic devices may be utilized for absorption of fluid in the treatment of a wound. In some embodiments, the use of multiple hemostatic devices may be advantageous in that the devices may be readily adjusted to any size, shape, or configuration of a wound by simply adding or removing individual hemostatic devices. Additionally, a higher degree of shape conformability may be obtained using, for example, multiple, small devices than with a single, larger device. A plurality of hemostatic devices may be carried in a small dispenser and could be extracted, as needed, and inserted into the wound. Alternatively, the devices may be packaged in a tightly rolled configuration, thus providing initially very thin swelling devices that could be inserted in the rolled-up configuration even into tight wound entries, such as bullet wounds, for example.

In some embodiments, devices of the invention may achieve enhanced swelling of the superabsorbent polymer particles by the inclusion of a plurality of hemostatic units in a single hemostatic device to increase the total surface area of superabsorbent polymer particles exposed to fluid relative to a hemostatic device having the same quantity of absorbent material but in a single hemostatic unit. This "compartmentalization" of multiple hemostatic units within a single device can allow for more efficient absorption of fluid. For example, such a device may comprise at least one porous membrane formed into an enclosure having an interior and an exterior, and a plurality of hemostatic units contained in the interior of the enclosure, wherein each hemostatic unit contains a plurality of polymer particles collectively forming a polymeric mass that are configured to swell in the presence of a fluid. Some or all of the hemostatic units may optionally comprise wicking elements capable of transporting fluid into an interior region of the polymeric mass of the unit.

Figure 4A:
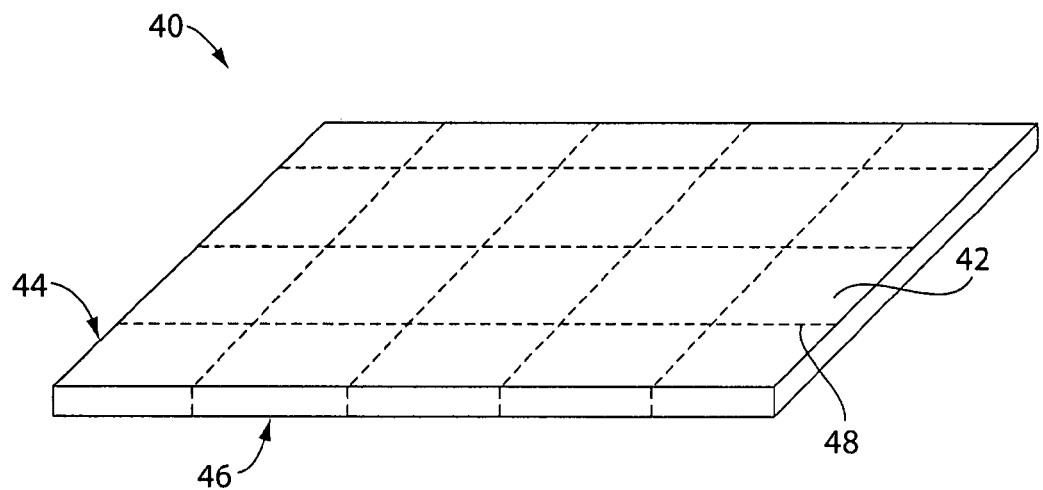
FIGS. 4A-B show hemostatic devices containing a plurality of swellable hemostatic units, according to certain embodiments of the invention.

In one embodiment, a hemostatic device can comprise a first porous membrane and a second porous membrane sealed together at selected locations to form a plurality of compartments, wherein each compartment comprises a hemostatic unit, as shown in FIG. 4A. Hemostatic device 40 contains a plurality of individual hemostatic units 42, each formed by sealing a portion of membrane 44 to a portion of membrane 46 to form sealing borders 48 defining the compartments. Each hemostatic unit 42 may comprise a plurality of superabsorbent polymer particles, as described above. The hemostatic device 40 can be folded as required to have a similar effect as, for example, the insertion of multiple smaller hemostatic devices, or can simply be laid over a wound opening and then pushed in to ensure contact all around the wound surface with excess device material simply protruding from the wound. In some embodiments, the sealing borders between individual hemostatic units may comprise perforations to act as a tear-off device, allowing the device size to be tailored as needed.

Figure 4B:
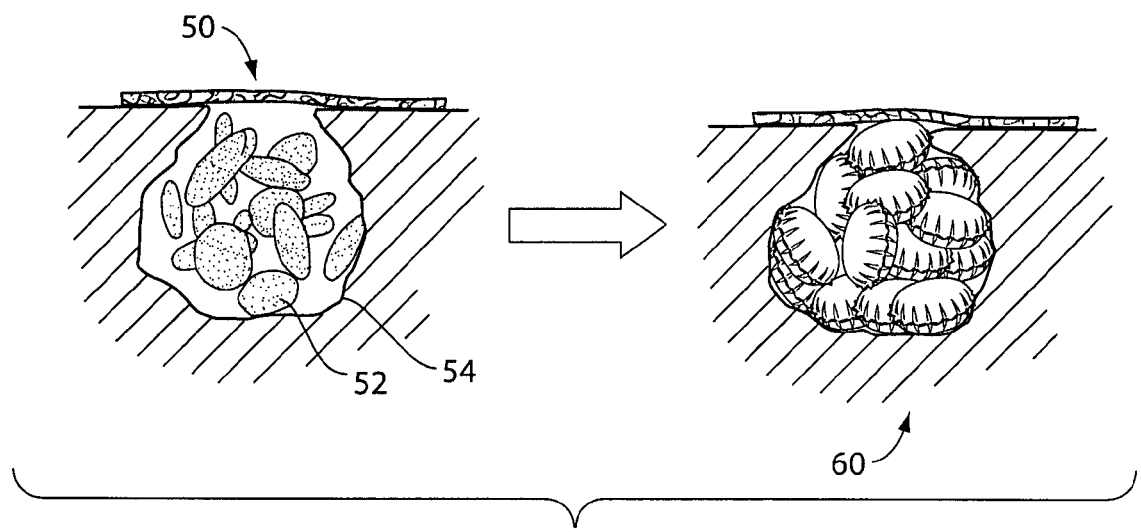

In another embodiment, illustrated in FIG. 4B, a hemostatic device 50 may comprise a plurality of hemostatic units 52, wherein each hemostatic unit comprises at least one porous membrane forming an enclosure that has an interior containing absorbent polymer particles. The hemostatic units may be, in turn, contained within the interior of an enclosure formed by another membrane or other porous material or net-like structure. Hemostatic device 50 comprises a plurality of hemostatic units 52 contained in a membrane enclosure 54. Upon contact with a fluid (e.g., blood), hemostatic device 50' adopts a swollen configuration 60.

In some cases, the hemostatic units may achieve acceptable swelling properties without addition of wicking elements, since increasing the total surface area of polymer particles exposed to blood (e.g., via "compartmentalizing") can reduce the depth of fluid penetration required to wet the polymeric mass throughout. Also, faster absorption of fluid may be achieved by compartmentalization. In some cases, the swelling and consequent exertion of pressure may be obtained through a largely inelastic geometry change of a number of smaller hemostatic units, which, when acting together, produce a single device capable of swelling to between 30 and 50 times its original volume.

It should be understood that, in some cases, it may be preferred that the individual hemostatic units further comprise wicking fibers, as described herein, to combine the effects of both the capillary action of the wicking fibers with the increase in exposed surface area provided by the compartmentalization techniques described above.

Without being bound by any particular theory or mechanism of action, it is believed that, the physical swelling function with this "compartmentalized" design may occurs at three levels. At the most basic level, the swelling is believed to driven by the absorption of fluid through outer membrane 54 of the device and into the individual hemostat elements 52 contained within the device. In such embodiments, wicking fibers may not be required since the polymer volume in each hemostatic unit may be small enough to be able to absorb and swell fully before gelling/coagulation of fluid on the surface of membrane 54 and/or the hemostatic unit occurs. At the next level, each hemostatic unit may swell to a maximum bloat driven by the polymer within and reach a maximum swollen size, thereby acting as an independent swelling element of the overall hemostatic device. At the uppermost level, a number of these independent hemostatic units interact with each other within a confined space, defined by the enclosure formed by the outer membrane of the overall hemostatic device. Initially, each hemostatic unit may be free to expand, but as they gain volume, they begin to exert pressure on each other. At this level the device begins to act as a single unit, capable of exerting and transferring pressure throughout its external geometry. This approach presents a potentially significant advantage for enhancing swelling speed. By dividing the polymer mass into discrete hemostatic units, the polymer is distributed more evenly through the wound than it would be if it was contained in a single mass without wicking filler. This can result in a much larger surface area of exposed polymer, which can significantly increase swelling speed. With this approach the swelling speed to maximum bloat of the individual hemostatic units has been measured to be less than 30 seconds for certain geometries. Since this swelling happens throughout the overall hemostatic device, the overall hemostatic device itself can bloat, for example to its maximum bloat, in less than 30 seconds, potentially giving it the capability to grow at a rate of between 600% and 1000% per minute. Furthermore, the addition of wicking elements, such as wicking fibers, in the hemostatic units may also result in a further increase in swelling speed.

As described herein, the plurality of hemostatic units may be contained in a porous container or enclosure. In some cases, the enclosure may be formed of a membrane that may be a highly stretchable membrane or net-like structure, which would not substantially limit the expansion of the device as a whole, but which would contain the hemostatic units in a single device. Such a membrane or net may be made of any suitable material; in certain embodiments, it may be formed of a biocompatible and highly elastic polymer. Such suitable polymers are well known to those skilled in the art and are commercially available. In other cases, the membrane may be formed of substantially non-stretchable membrane, but may be sized to provide an enclosure with enough excess volume, so that it does not substantially limit the expansion of the hemostatic device as a whole.

The hemostatic units can be made in any suitable size such that they may be contained with an enclosure or container of a desired size. For example, for larger wounds, the size of the individual hemostatic units may be at least 20 mm in diameter before swelling, and the membrane enclosure containing the plurality of these elements may, for example, be an essentially square enclosure at least 20 mm×20 mm in size. Of course, the size of the membrane enclosure may be selected and varied, as would be apparent to those skilled in the art, to provide sufficient volume to accommodate a desired number of hemostatic units of a particular size, accounting for the degree of swelling of the hemostatic units and given the maximum degree of stretch of the membrane material. Similarly, membrane enclosures of various shapes may be provided, depending on the type of wound to be treated, etc., as would be apparent to those skilled in the art. For example, for smaller wounds, the individual hemostatic units may be 5 mm in diameter and the membrane containing the plurality of these elements may be at least 5 mm×5 mm, depending on the factors noted above. It should be understood that the device may have any size or shape required to suit a particular application.

Another advantageous feature of certain devices and methods of the invention is the ability to provide for the three-dimensional absorption of fluid. While many known absorbing devices are limited to a two dimensional geometry, resulting in planar transport, certain devices and methods disclosed herein can provide three-dimensional flow of fluid through the device, resulting in more efficient absorption of fluid and, therefore, more efficient exertion of pressure on a wound and/or sealing of the wound.

Figure 5:
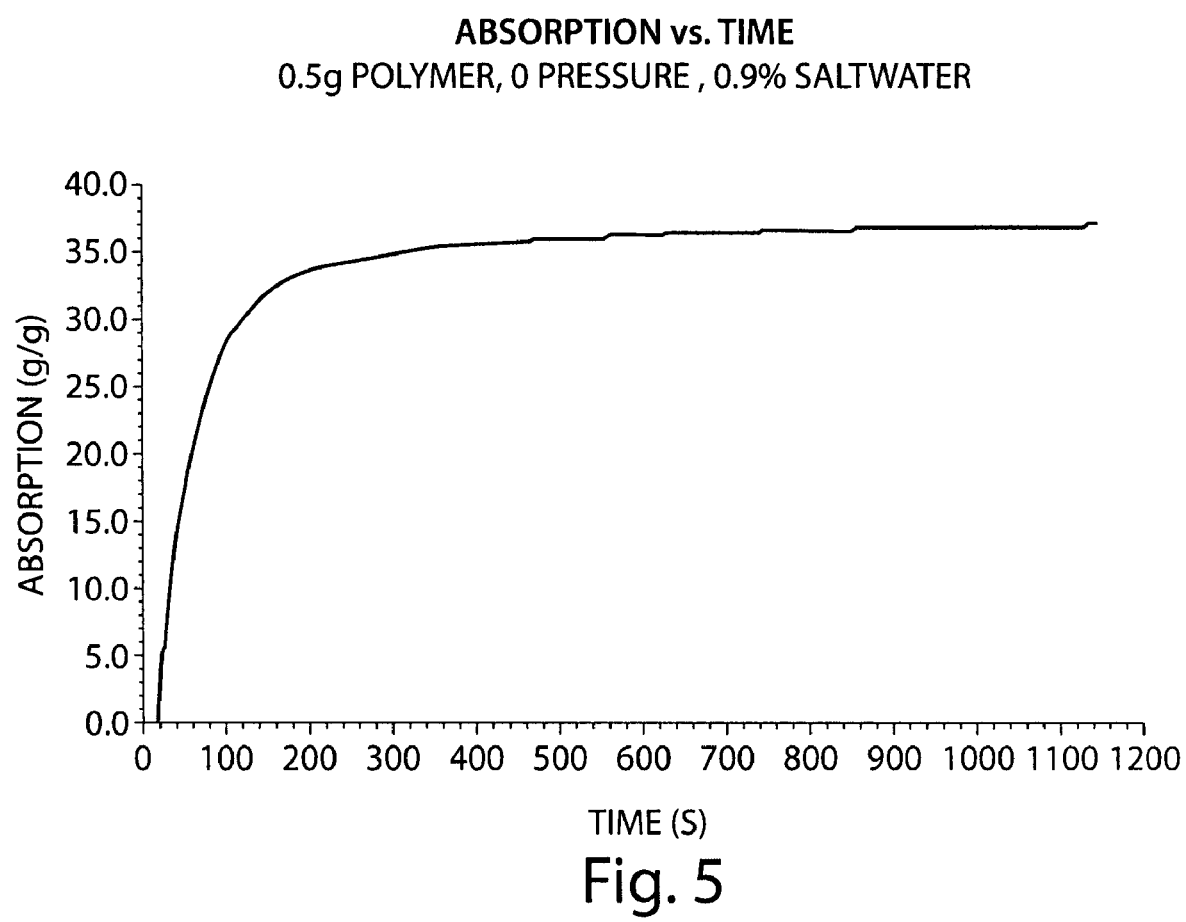
FIG. 5 is a graph showing the free swell absorption kinetics of a superabsorbent polymer in 0.9% salt water solution, according to one embodiment of the invention.
Figure 6:
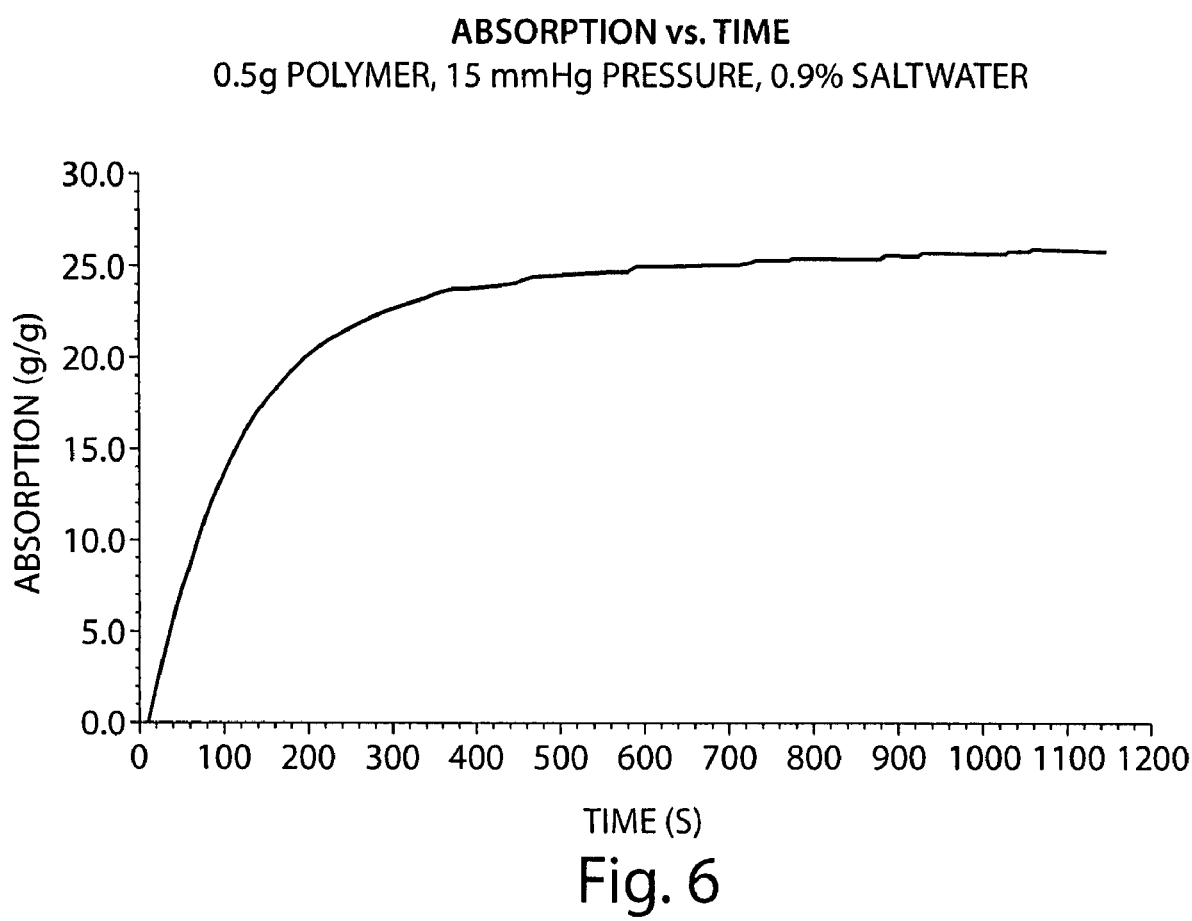
FIG. 6 is a graph showing the absorption kinetics of a superabsorbent polymer in 0.9% salt water solution under a pressure equivalent to 15 mm Hg, according to one embodiment of the invention.
Figure 7:
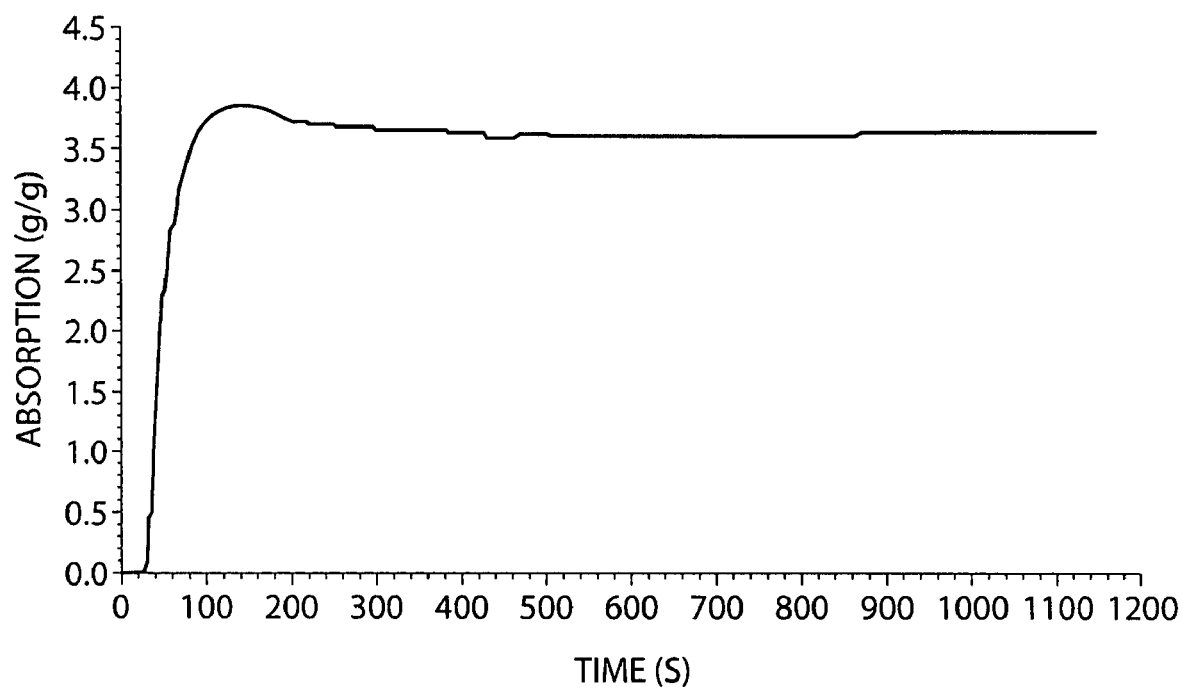
FIG. 7 is a graph showing the absorption kinetics of a superabsorbent polymer in 0.9% salt water solution under a pressure equivalent to 60 mm Hg, according to one embodiment of the invention.

Absorption rates of certain hemostatic devices described herein may be at least 20 to 21 grams, or more, of blood per gram of polymer within 5 minutes (or, in some cases, more than 5 minutes) in free-swelling conditions. This represents an average swelling rate of at least 400% per minute in blood in free swelling conditions. Typical absorption rates of certain devices, when swollen in deionized water in free-swelling conditions can achieve swelling ratios of as high as 140 grains of water per grain of polymer in 3 minutes, representing an average swell ratio of 4500% per minute. This comparison demonstrates the preference to conduct testing of hemostatic devices in blood rather than water. Experimental data indicate that the swell behavior appears to be essentially exponential, and the majority of swelling takes place soon after immersion of the device in the fluid. It has also been observed that external pressure tends to have a significant effect on the swelling ratio, as swelling can depend strongly on the balance between internal pressure within the device and external pressure. Typical polymer swelling curves in 0.9% salt water, which mimics the salinity of human blood, are shown in FIGS. 5-7 for blends of sodium polyacrylate polymers comprising high surface area particles and poly-anionic beads in a 1:1 ratio. FIG. 5 is a graph of the swelling curve for the sodium polyacrylate polymer blend in 0.9% salt water at 0 mm Hg pressure. FIG. 6 is a graph of the swelling curve for the sodium polyacrylate polymer blend in 0.9% salt water at 15 mm Hg pressure. FIG. 7 is a graph of the swelling curve for the sodium polyacrylate polymer blend in 0.9% salt water at 60 mm Hg pressure. Different results can be achieved by varying the ratio of the polymer blend components.

Another aspect of the present invention provides methods for treating wounds using one or more hemostatic devices, as described herein. Such methods may involve inserting one or more hemostatic devices into, near, or onto the surface of a wound.

Superabsorbent polymers and polymer particles that may be used in the present invention to form hemostatic devices may be selected and/or designed to exert substantial pressure to/within a wound upon swelling and/or form a tight seal, pressure effective enough, for example, to stop high pressure bleeding from transected principal arteries. The polymer may be used as an actuating and sealing element, and, in some cases, may preferably be a superabsorbent hydrogel. These polymers, for example polymers based on sodium polyacrylate, are known to be able to absorb hundreds of times their weight in fluid.

A short description of the properties and behavior of certain hydrogels is provided below, which hydrogels may be suitable for use in certain embodiments of the hemostatic device discussed herein. It should be noted that the list is not exhaustive, and those of ordinary skill in the art may readily select or form other suitable absorbent materials using available information regarding the absorbency and swelling properties of various materials and no more than routine experimentation and screening tests.

Polymer gels are typically characterized by long chain polymer molecules that are crosslinked to form a network. This network can trap and hold fluid, which can give gels properties somewhere between those of solids and liquids. Depending on the level of crosslinking, various properties of a particular gel can be tailored. For example, a highly crosslinked gel generally is structurally strong and tends to resist releasing fluid under pressure, but may exhibit slow transition times. A lightly crosslinked gel may be weaker structurally, but may react more quickly during its phase transition. In the design of gels for a particular application, the degree of crosslinking may be adjusted to achieve the desired compromise between speed of absorption and level of structural integrity. Those of ordinary skill in the art would be able to identify methods for modulating the degree of crosslinking in such gels.

A property of gels in powder form that may be particularly useful in the present invention is their ability to block flow of fluid and/or gas. Gels in powder form, when dry, can allow the passage of air and water in spaces that exist between the packed particles, provided the particles are of sufficient size to produce sufficiently large spaces However, when this powder mass is brought into contact with a fluid medium such as water, the particles at the surface of the mass begin to absorb fluid, swell, and soften. If the motion of the gels is somewhat restrained by restricting an overall change in volume, the swelling particles can fill in the empty spaces between the particles, effectively sealing off the flow path.

As long as fluid medium is present, the gel tends to swell to regain a condition of equilibrium, which can ensure that the seal is maintained. In certain embodiments of the present invention, fast swelling superabsorbent polymers are used in the creation of a hemostatic device that is activated by the presence of water, either fresh water or water with a sodium ion concentration ranging from about 0 to 10%. Such properties enable the polymer to swell in the presence of blood by absorbing the water content of the blood while tolerating the presence of a significant concentration of other species in blood, such as sodium ions, for example.

The nature of the fluid, more specifically the concentration of sodium ions, in part, determines the degree of absorption and swelling ratio. For example, the polymer may absorb 400 to 500 times its weight in distilled or deionized water, but this may drop to 100 times if the water is ordinary tap water, or 50 times or less if the water has a significant content of sodium ions. This is because the water absorption is driven by a property called osmotic pressure, which the polymer strives to maintain balanced at zero differential with respect to the surrounding environment. Osmotic pressure at equilibrium has been shown to be related to a combination of the rubber elasticity of the polymer network, the polymer-polymer and polymer-solvent affinity, and the ionization of the polymer network. The rubber elasticity of the network can provide a mechanical restoring force to changes in volume. The affinity of the polymer for itself and the solvent can determine whether this component of osmotic pressure drives it to absorb fluid or not. Finally, the ionization of the network can determine the driving force that attempts to balance the ionization level of the polymer with that of the solvent in the surroundings. The ionization of the polymer network can provide the opportunity to tailor the polymer's behavior. By modifying the ionization of the polymer it is possible to affect the types of fluids that can be absorbed and the degree to which they are absorbed. For a given ionization, if the fluid contains a higher ionic concentration than the polymer, this component would not tend to drive absorption. On the other hand, if the fluid is deionized water, the driving force for absorption would be greater and the swelling ratio correspondingly large.

In some embodiments, the polymer particles comprise polyacrylates. For example, sodium polyacrylate-based superabsorbent polymers can be modified to provide polymer particles having a greater affinity for sodium ions than the sodium ions have for water. In an illustrative embodiment, a polyacrylate-based superabsorbent polymer with convoluted surface topology is used. This polymer is commercially available in various suitable forms. In some cases, the polymer may be a blend of a commercially available sodium polyacrylate polymer with poly-anionic beads (PAB), as supplied by Champion Enterprises, Ft. Wayne, Ind., that have an affinity for sodium ions, and a surfactant, humectant, or other agent that assists in the absorption of water. Since the blend can be tailored to suit the application, and each component is useful depending on the application, the range of blend ratios can be between about 0% and 100% of sodium polyacrylate and PAB, for example, 0:100, 1:99, 2:98, 3:97, and so on. According to the present invention, one suitable ratio is 50:50, i.e. approximately equal parts of sodium polyacrylate polymer and PAB. Such a polymer blend can exhibit suitable speed and swelling ratio requirements for functioning in blood. In some cases, certain blends of the sodium polyacrylate polymer and PABs can tolerate very high sodium ion concentrations, e.g. up to about 10% sodium ions, including levels found typically in blood. Such polymers may be provided in powder form with average particle sizes ranging, for example, between 1 micron and 1000 microns, or, in some cases, between 200 microns and 400 microns. The average particle size may be determined by fractionating the polymer using sieves that encompass the minimum and maximum sizes of the desired size range in order to exclude particles outside the desired size range. In some cases, the polymer particle size is selected such that, when contained in hemostatic devices of the invention, the polymer particles may expand freely and completely, but may be prevented from escaping into the blood stream through the walls of an enclosure containing them, as described more fully below. Typical swelling kinetics curves for the polymers used in this invention, in 0.9% salt water, are shown in FIGS. 5-6.

As used herein, "particle size" refers to the largest characteristic dimension (i.e. of a line passing through the geometric center of the particle e.g., diameter) that can be measured along any orientation of a particle (e.g., a polymer particle). Particle size as used herein may be measured or estimated, for example, using a sieve analysis, wherein particles are passed through openings of a standard size in a screen. The particle-size distribution may be reported as the weight percentage of particles retained on each of a series of standard sieves of decreasing size, and the percentage of particles passed of the finest size. That is, the average particle size may correspond to the 50% point in the weight distribution of particles.

It will be apparent to those skilled in the art that a wide range of swellable polymers can be used in devices and methods of the present invention, depending on the desired performance and intended use. For example, polysaccharides, isopropylacrylamides, and/or butylacrylamides may also be used within the context of the invention. Sodium polyacrylate polymers have been used in diapers and other absorbent devices for many years because they have a high swelling capability, can swell in a matter of seconds, retain the fluid effectively under pressure, and generally show no adverse reaction on the human body.

Wicking elements that may be suitable for use in the present invention include, but are not limited to, fibers such as Nylon fibers, highly convoluted wicking PET fibers, polypropylene fibrous filler material, other hydrophilic materials capable of transporting fluids via capillary action, and the like. Wicking elements may be hydrophilic, or coated or otherwise treated to render them or at least their surfaces hydrophilic. Those of ordinary skill in the art would be able to select appropriate materials to provide wicking elements for use in the present invention based on the teaching and direction provided herein. A screening test for suitable wicking materials may involve immersing an enclosed structure (e.g, a membrane(s) forming an enclosure(s)) containing a hydrophilic material wicking element candidate and swellable polymer material in a fluid and examining the swollen material to determine whether or not the hydrophilic material successfully transported fluid to the interior portions of the structure. This may be accomplished by, for example, cutting the swollen structure in half to examine the difference between the portions close to the surface of the structure and the portions in the interior of the structure.

As described herein, wicking fibers and polymer particles may be combined together to produce the hemostat devices. In some cases, a device comprises a plurality of wicking fibers and a plurality of polymer particles which interact to form a polymeric mass, which is in the form of a fibrous structure. The interaction may involve covalent bonding, ionic bonding, hydrogen bonding, dative bonding, electrostatic interactions, van der Waals interactions, other types of bonding or interactions, and/or the like. In some cases, at least a portion of the plurality of absorbent polymer particles are bonded to at least a portion of the plurality of wicking elements. Such bonding may produce a fibrous structure comprising intertwined fibers with polymer particles bonded to the fibers. The bonding between wicking fibers and polymer particles can also provide sufficient spacing between polymer particles to facilitate and/or maximize fluid absorption throughout the device.

The wicking fibers and polymer particles may be combined alone, or in the presence of additional materials, such as bonding agents (e.g., propylene glycol, adhesives, etc.), solvents, and the like. Those of ordinary skill in the art would be able to identify materials and methods suitable for use in the formation of structures comprising wicking fibers and polymer particles, as described herein. For example, the wicking fibers, polymer particles, and at least one bonding agent may be combined, such that a cohesive structure is formed and/or sufficient bonding between wicking fibers and polymer particles occurs, without reducing or diminishing the absorption properties of the structure (e.g., by encapsulating the polymer).

In some embodiments, wicking fibers are used, wherein the diameter of the wicking fibers may preferably be in the range of approximately 10-150 microns. The blending of wicking fibers and polymer particles may be performed by mixing them together in the presence of a bonding agent, such as propylene glycol, for example in a mass ratio of approximately 1:10 (fiber:polymer) with the polymer particles. This may be achieved by dissolving the propylene glycol in a sufficient quantity of alcohol, mixing with the polymer particles, and allowing the alcohol to evaporate. The polymer particles become coated with a small amount of propylene glycol, and are then added to the wicking fibers and shaken in a closed container, resulting in an evenly distributed cloud of polymer particles within a fibrous structure. As described here, the fibrous structure may maintain spacing between the polymer particles, which, when combined with the capillary action of the wicking fibers, increases the area for fluid flow to ensure complete absorption and swelling. Those of ordinary skill in the art would be able to select additional methods and materials for bonding of polymer particles to fibers.

The mass ratio of polymer particles to wicking elements may be such that the wicking paths are maintained for a sufficiently long enough time to enable the entire polymeric mass in the hemostatic device to swell. In some embodiments, the preferred blend ratio of wicking element mass to polymer particle mass ranges from approximately 1:10 to 1:2, with a ratio of 3 grams of wicking element to 10 grams of polymer particles being one example. In one embodiment, the mass ratio of wicking elements to polymer particles is 1:3.3. Devices of the invention may advantageously maintain a high ratio of absorbing material mass (e.g., superabsorbent polymer particle mass) to wicking element mass.

Membranes used for containing swelling materials and, optionally, wicking fibers as described herein, or for containing multiple hemostatic units in a multi-unit device, may be selected to suit a particular application. The membranes may comprise an elastic material or a sufficiently sized non-elastic material, such that the membrane may enable swelling of the polymer particles, and the device may undergo a change in size and/or shape upon absorption of a fluid (e.g., blood), but may also be resistant to tearing and/or puncturing. For example, in some cases, the membrane may be an elastic material that may stretch in accordance with the swelling polymer particles enclosed within the membrane. Examples of such elastic materials include, for example, polyisoprene, polybutadiene, polydimethyl siloxane, latex rubber, and copolymer materials, such as copolymers of polyurethane and polyethlyene glycol (Lycra), and the like. In some cases, the membranes are made from a non-stretch or substantially non-elastic material. In such cases, the membranes may then be configured and sized such that the device may still undergo a change in size and/or shape. For example, the device may be provided such that there is excess non-elastic material which can be folded or rolled, and, upon absorption of fluid, the device may swell and increase in size. Examples of suitable non-elastic membrane materials include nylon, polypropylene, polyethylene, polyethylene terephthalate (PET), polycarbonate, acrylic polymers, polystyrene, cellulose or cellulose esters, polysulfone, or the like. In certain embodiments, the membrane may be in the form of a continuous sheet that comprises a plurality of pores therethrough. In other embodiments, the membrane may comprise a plurality of fibers, configured, for example in the form of a non-woven felt or matt or, alternatively, in the form of a knitted or woven fabric or in the form of a screen.

Membranes suitable for use in the present invention may also contain pores or other openings through the membrane to facilitate more rapid passage of fluid through the membrane. A wide variety of suitable membrane materials having a wide variety of average pore size and pore size distribution are readily commercially available from a number of suppliers. In some cases, the pores of the membrane may be sufficiently small to contain the polymer, or polymer and wicking fiber mixture, without leakage, while sufficiently large to enable free fluid flow. In some cases, the membrane may possess pores large enough to enable the uninhibited flow of blood. In some embodiments, the pore size may be larger than the size of the polymer particles, for example, if the polymer particles are blended with materials (e.g., wicking fibers) such that the blend is bonded together and thereby able to be contained. Also, while the use of larger pore sizes may result in the loss of a small number of particles through the membrane, the blood pressure gradient within the wound cavity may ensure that any particles that are lost from the device will remain in or near the wound cavity. Moreover, even in the absence of such pressure, blood vessels will normally collapse, thereby effectively preventing the entrance of loose particles into the circulatory system even if they did leak from the membrane. In some cases, the membrane is a microporous membrane. In some cases, the membrane may contain pores having an effective average diameter of about 0.15 mm to 1.0 mm, more preferably 0.2 mm-0.5 mm. Pore sizes of the membranes may be measured by, for example, a microscope, via a porometer device, via particle retention tests, or otherwise, as would be apparent to those skilled in the art. Nominal pore size for a particular membrane material is typically specified by the manufacturer and supplier of the commercially available membrane materials.

The membrane may be formed from a single continuous piece or a plurality of joined pieces. For example, at least two membranes can be joined along their outer edges, with the swelling materials contained inside. Alternatively, a single membrane can be folded or otherwise formed into an enclosure for containing polymer particles in its interior.

Other characteristics that may be desirable for materials used as membranes in the present invention include hydrophilicity, biocompatibility, sufficient elasticity without excessive stiffness, and the ability to seal the membrane to itself or other membranes using conventional industrial methods.

In an illustrative embodiment, a commercially available, honeycomb knit Lycra fabric may be selected as the membrane. For example, SL-485 Micro Mesh Lycra, available from various suppliers, which is a blend of 80% Polyester and 20% Lycra, with a stretch of 25% in width and 50% in length, may be selected as the membrane. It should be understood that other commercially available or custom made membranes may also be used.

A number of alternative designs for achieving constructions that enable wicking and/or absorption of blood into a hemostatic device are possible. In some embodiments, a single layer or multiple layers of superabsorbent polymer may be bonded to a strip of material (e.g., a hydrophilic fabric strip) located in the interior of the device with a surfactant or water-soluble adhesive. Similarly, in another embodiment, the polymers may be bonded to an interior surface of a surrounding membrane of the device with a surfactant or water soluble adhesive. Such approaches may provide as extensive a polymer surface as possible inside the device such that the maximum amount of polymer may contact the fluid, while reducing the length of the path the fluid has to travel in order to make contact with the polymer. Also, bonding the polymer to a surface within the device may prevent it from agglomerating. This may enable a more effective infiltration of fluid into the polymeric mass.

These above descriptions of applications for the inventive devices are not intended to be exhaustive, and merely illustrate some of the possible embodiments and uses of this invention. It will be apparent to those skilled in the art that certain embodiments of this invention may be well suited for the temporary emergency plugging of any leak within the pressure range of the device in which water, seawater, or other solvent able to swell the absorbent material, forms at least part of the leaking fluid. It will also be apparent to those skilled in the art that by utilizing polymers that swell in the presence of organic compounds, the device may be employed in instances where the leaking fluid is gasoline or oil, for example.

The function and advantage of these and other embodiments of the present invention may be more fully understood from the examples below. The following examples, while illustrative of certain embodiments of the invention, do not exemplify the full scope of the invention.

EXAMPLES

Example 1

Manufacture of Hemostatic Device

A hemostatic device was tested on an animal using a Fatal Groin Injury Model, as described below. During this test four hemostats were used, although any suitable number may be used. The hemostats used comprised a 4"×4" SL-485 Micro Mesh Lycra bag containing 10 grams of a 50-50 blend of sodium polyacrylate superabsorbent polymers in two forms. One form is a high surface area particle of arbitrary shape, which provides speed and initial volume swell, and the other form is a poly-anionic bead form, which provides structural integrity and pressure (supplied by Champion Enterprises, Ft. Wayne, Ind.). The blend was then treated with 1 gram of propylene glycol—and 3.3 grams of polypropylene fluff filler. The hemostatic devices weighed 15 grams each.

The hemostatic devices were manufactured by enclosing a blend of polymer and fiber, as described herein, in a bag formed by bonding two 10 cm by 10 cm sheets of Lycra knit fabric. It should be clear that this size and weight were selected for the purposes of testing and that the sizes, contents and ratios can be scaled up or down to suit any alternative application, test or wound type. The typical construction and construction process used in prototyping the preferred embodiment of this device involves forming a blend of the propylene fibers with sodium polyacrylate superabsorbent polymer particles attached to fibers using the propylene glycol. The polymer and fiber composite is then inserted into the Lycra bag, which was then either sealed with a latex-based adhesive, to form the final hemostatic device. Alternatively, the bag may be heat-sealed, wherein fabric stretch and other performance characteristics may be substantially retained since the heat seal takes place fiber on fiber.

Example 2

Live Testing of the Hemostatic Device

A pig (46.3 kg) was anesthetized and instrumented at the neck to read all relevant vital signs. Ports were inserted for the introduction of fluids. A complex groin injury was inflicted to produce uncontrolled hemorrhage. This injury included transaction of the proximal thigh soft tissues (skin, quadriceps and adductor muscles), and complete division of the femoral artery and vein just below the inguinal ligament. This was achieved by incising these structures with a sharp scalpel (as described in, Alam, H. B., et al., "Application of a Zeolite Hemostatic Agent Achieves 100% Survival in a Lethal Model of Complex Groin Injury in Swine," *J Trauma*, Vol. 56, No. 5, May 2004, incorporated herein by reference).

The wound was produced and bleeding was allowed to occur freely. After 3 minutes of uncontrolled bleeding, the four test hemostatic devices constructed as described in Example 1 were inserted into the wound. Once the hemostats were in place, a standard gauze dressing (67 grams) was used to pack the wound. Subsequently, manual compression was applied for 5 minutes, after which pressure was removed and the wound was observed. Fluid resuscitation began 15 minutes after the initial creation of the injury, and the pig received 2 liters of standard 0.9% saline solution, administered intravenously, over a period of 30 minutes. The pig was monitored for a total of 120 minutes after the time of injury. Midway through the experiment, the swelling of the hemostatic devices was apparent. At the end of the experiment the pig was euthanized. At the completion of the test, the swelling had forced the gauze bandage out of the wound site. The top of the bandages remained dry even as blood pressure increased during resuscitation. After removal of the gauze bandages at the end of the test, the hemostats were removed and studied. Bleeding vessels had to be clamped off as the hemostatic devices were removed to prevent further bleeding.

The devices, which had been removed from the wound site, were observed to absorb blood throughout the device, as observed by examination of the swollen polymeric material.

Blood loss during the initial 3 minutes was measured continuously by suctioning the blood into a collection container. Blood loss during the remainder of the test (3-120 minutes) was measured by weighing all the dressings before and after the experiment and adding the difference to the total blood loss. The blood loss is shown in Table 1.

Figure 8:
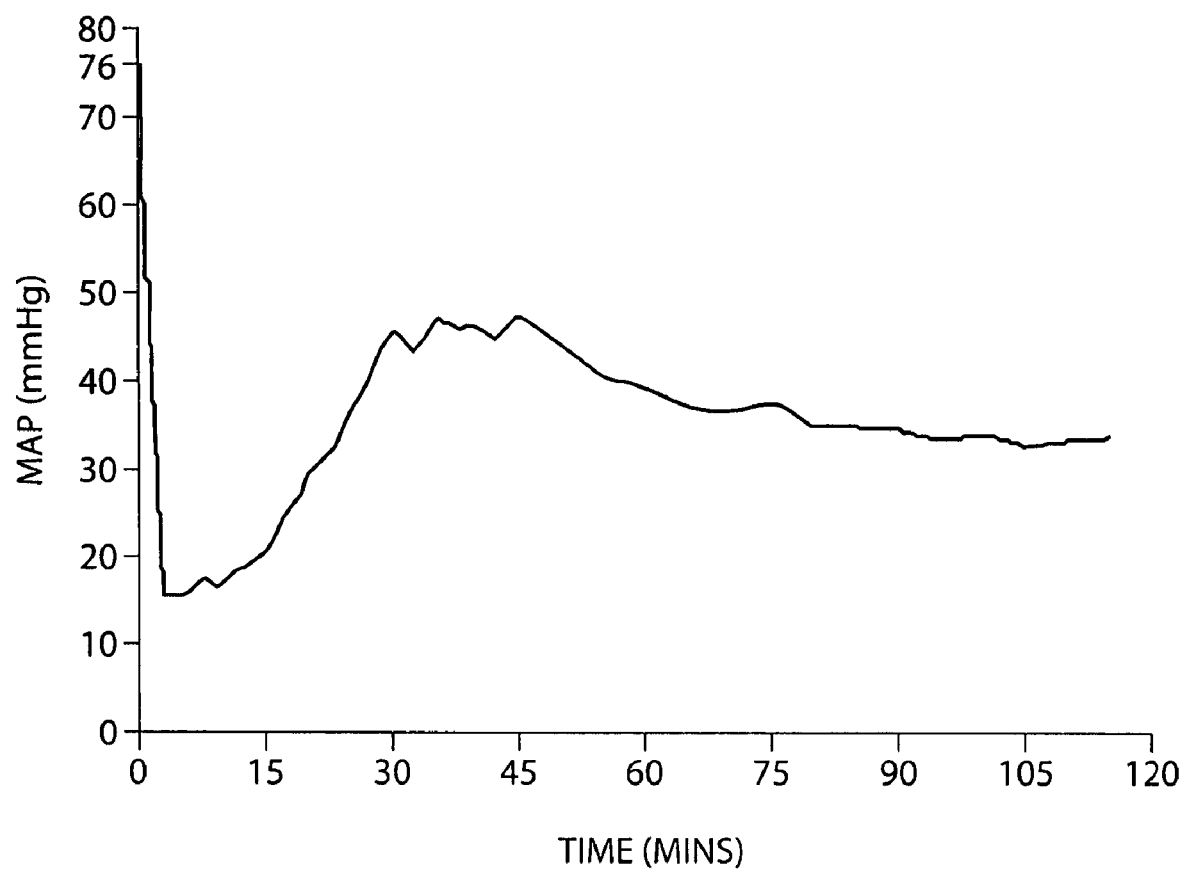
FIG. 8 is a graph showing the Mean Arterial Pressure (MAP) measured during the test treatment method described in Example 2.

Blood pressure was monitored throughout the duration of the test. The mean arterial pressure (MAP) was calculated using the formula $(2*D+S)/3$, where D is the diastolic pressure and S is the systolic pressure. FIG. 8 shows a graph of the MAP measured during the test treatment method described in this example.

The hemostats showed an excellent ability to control and stop the bleeding even after increasing the blood pressure with the resuscitation fluids. Throughout the test, there was clear visual evidence of the devices swelling inside the cavity and applying pressure. Upon removal of the devices at the end of the test, several vessels inside the wound began bleeding heavily again, indicating that the hemostats were successfully sealing the bleeding sites the test. The pig survived the entire 120 minute duration of the experiment.

TABLE 1

Summary of blood loss and blood absorption by hemostats

|  | Initial weight (g) | Final weight (g) | Net blood absorbed (g) | Blood loss (ml) (1 g ≈ 0.95 ml) | Normalized blood loss (ml/kg body wt) |
|---|---|---|---|---|---|
| Initial blood loss | — | — | — | 812 | 17.5 |
| Standard gauze | 67 | 110 | 43 | 41 | — |
| Hemostat #1 | 15 | 83 | 68 | 65 | — |
| Hemostat #2 | 15 | 76 | 61 | 58 | — |
| Hemostat #3 | 15 | 134 | 119 | 113 | — |
| Hemostat #4 | 15 | 69 | 54 | 51 | — |
| Total absorption | — | — | — | 328 | 7.1 |

Example 3

Clinical Testing of the Hemostatic Device—Complete Vessel Transection

A hemostatic device, as described in Example 1, was tested in 20 pigs using a model of fatal groin injury developed by Alam (as described in, Alarm, H. B., et al., "Application of a Zeolite Hemostatic Agent Achieves 100% Survival in a Lethal Model of Complex Groin Injury in Swine," *J Trauma*, Vol. 56, No. 5, May 2004, incorporated herein by reference), inflicted under anaesthetic, to produce uncontrolled hemorrhage. The injury included transection of the proximal thigh soft tissues (skin, quadriceps and adductor muscles) and complete division of the femoral artery and vein just below the inguinal ligament. After injury, the animal was randomized into one of two groups, (a) a hemostat group and (b) a control group. The control group was treated using a standard gauze dressing and the hemostat group was treated using the hemostat with the standard gauze dressing. Three minutes of uncontrolled bleeding were allowed and then the wound was packed with either standard gauze dressing for the control group, or, hemostats and the standard gauze dressing for the hemostat group. Subsequently, manual compression was applied to the wound for 5 minutes, after which pressure was removed and the wound was observed. Fluid resuscitation was applied 15 minutes after the initial creation of the injury, and each pig received approximately 2 liters, adjusted for body weight, of standard 0.9% saline solution administered intravenously over a period of 30 minutes. Each pig was monitored for a total of 120 minutes after the time of injury. During the resuscitation and observation period, any reasonable procedure that could be applied in the field to ensure survival was applied as required. This was done to simulate field conditions as closely as possible. During the experiment a number of physiological indicators such as blood pressure, blood gas, and pulse were monitored and recorded for later interpretation. At the end of each experiment each pig was euthanized.

Figure 9:
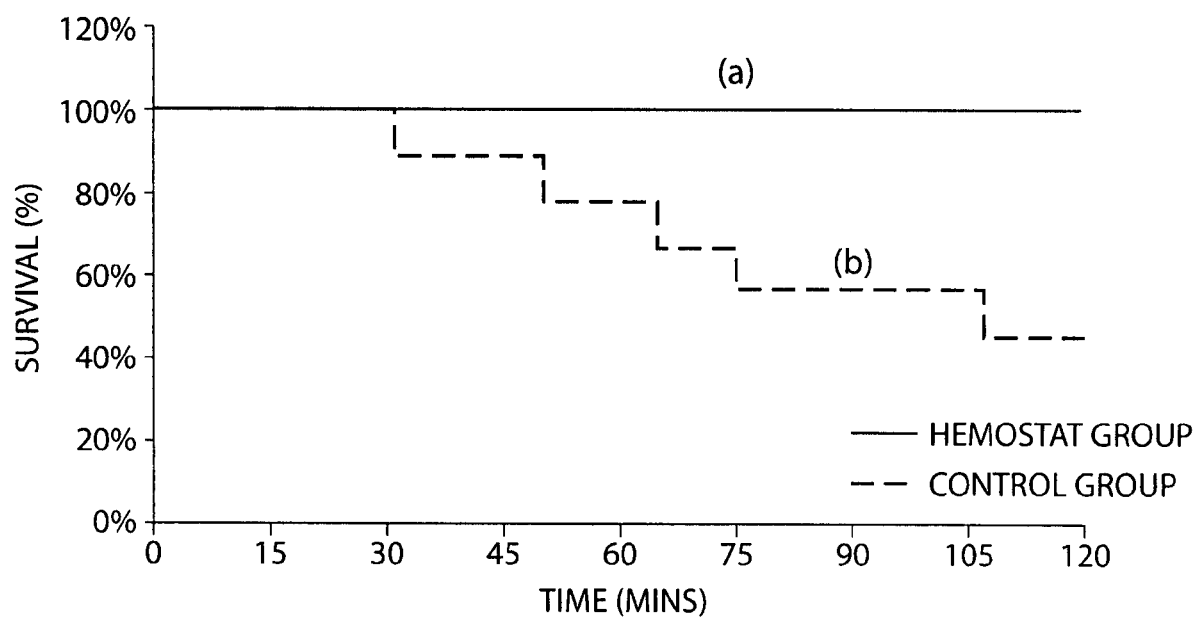
FIG. 9 is a graph showing the survival rates and time of death of animals having wounds treated with hemostatic devices of the invention for (a) the hemostat group and (b) the control group in Example 3.
Figure 10:
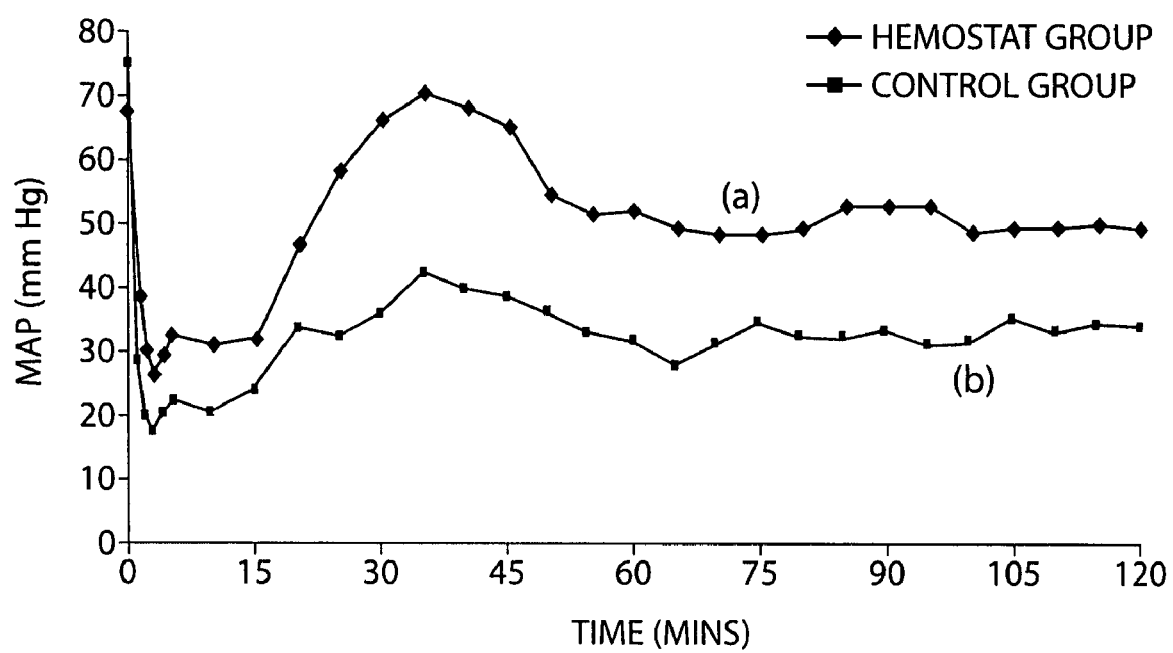
FIG. 10 is a graph showing the average of the mean arterial pressure for (a) the hemostat group and (b) the control group, measured over the duration of the experiments conducted in Example 3.

The data measured during the experiments was studied to highlight trends in device efficacy. The key indicator of device efficacy was the survival rate measured for both the control group and the hemostat group. FIG. 9 shows a graph of the survival rates and time of death of animals of (a) the hemostat group and (b) the control group. The control group, which counted n=9 animals, achieved a survival rate of 44% using the standard gauze dressing and standard resuscitation procedures. The hemostat group, which counted n=9 animals, achieved a survival rate of 100% by using the hemostat device, a standard dressing and standard resuscitation procedures. FIG. 10 shows a graph of the average of the mean arterial pressure for (a) the hemostat group and (b) the control group, measured over the duration of each experiment. The data for the control group showed the average only for the surviving animals, meaning that the calculation of the average at any point in time was done only for animals that survived at that time. For the surviving animals, the hemostat group showed a significantly higher average MAP, particularly in the early stages of resuscitation. This was a result of reduced post-treatment bleeding in the hemostat group and illustrated the efficacy of the hemostatic devices in stopping bleeding and holding pressure, which contributed to the overall high survival figures achieved in the hemostat group.

Figure 11:
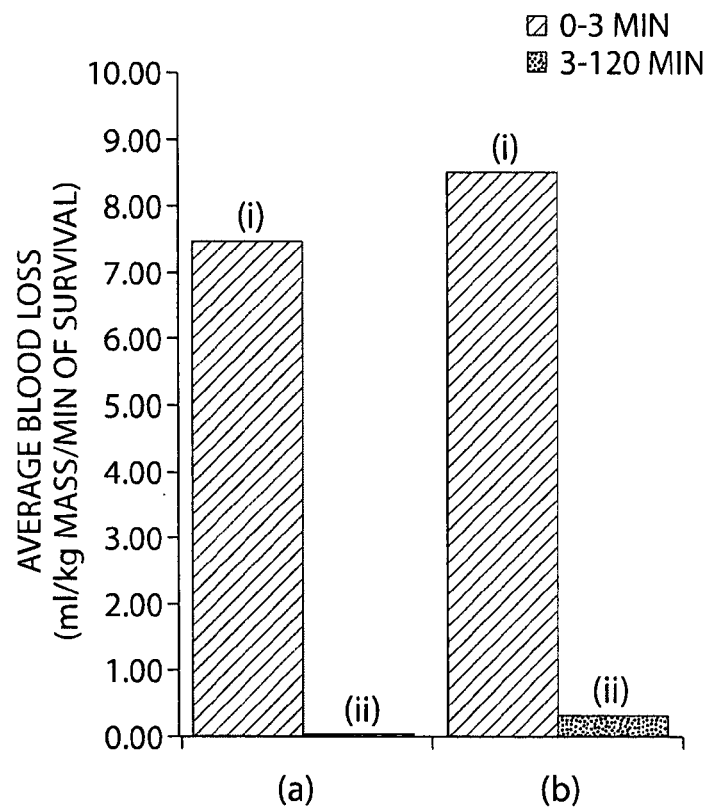
FIG. 11 is a graph describing the (i) pre-treatment and (ii) post-treatment mass and time normalized blood loss for (a) the hemostat group and (b) the control group in Example 3.
Figure 12:
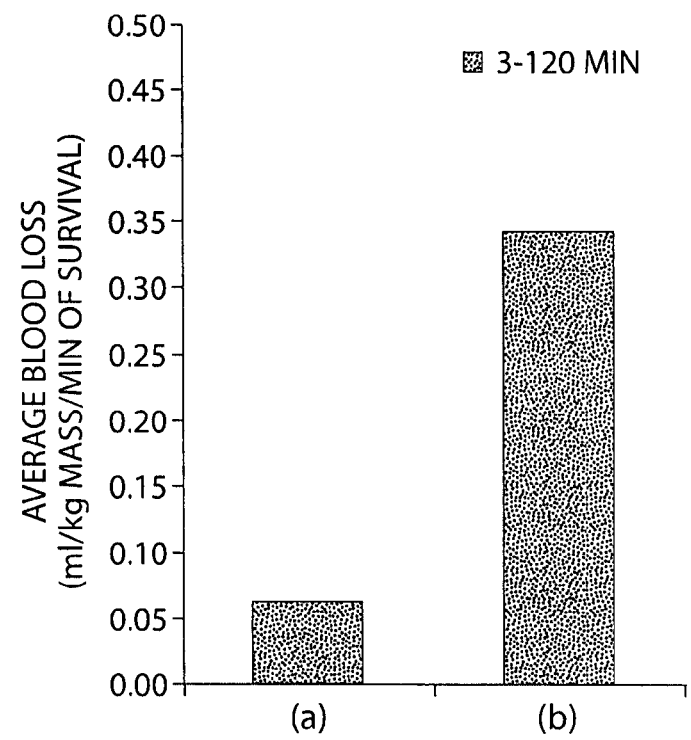
FIG. 12 is a graph describing the post-treatment blood loss for (a) the hemostat group and (b) the control group in Example 3.

The normalized blood loss (mass and time), measured before and after application of the wound dressings is summarized by the graphs in FIGS. 11-12. The pre-treatment blood loss (0-3 min) was obtained by dividing the total mass of blood collected before treatment by the mass of the animal and by the pre-treatment time. The post-treatment blood loss (3-120 min) was obtained by dividing the total mass of blood collected after start of treatment by the animal mass and the time to death, after removing the initial 3-minute period. This calculation accounted for the animals that died before the end of the experiment and, consequently, stopped bleeding (Ahuja et al, "Testing of Modified Zeolite Hemostatic Dressings in a Large Animal Model of Lethal Groin Injury," *Journal of Trauma, Injury, Infection, and Critical Care*, December 2006). The difference in post-treatment blood loss showed that the hemostat made a significant difference in its reduction.

FIG. 11 shows a graph describing the (i) pre-treatment and (ii) post-treatment mass and time normalized blood loss for (a) the hemostat group and (b) the control group. FIG. 12 shows a graph describing the post-treatment blood loss for (a) the hemostat group and (b) the control group. The post-treatment blood loss was scaled in FIG. 12 so that the relative difference between the hemostat and control groups could be more easily observed. The hemostat group, on average, bled one fifth of the amount measured in the control group after the application of treatment and resuscitation, clearly demonstrating the efficacy of the device.

The above results demonstrated that the swelling hemostat devices described herein work well in this swine model of lethal groin injury with complete transection of the femoral vessels. This was demonstrated by the difference in survival numbers (100% for the hemostat versus 44% for the control group), by the difference in post-treatment blood loss (0.06 ml/kg/min for the hemostat versus 0.34 ml/kg/min for the control group), and by the significantly higher MAP achieved during resuscitation by the hemostat group. No secondary side effects, such as exothermic heating, were observed. Additionally, there was no need for drying, wetting, cleaning, or other treatment of the wound site.

Example 4

Clinical Testing of the Hemostatic Device During Partial Vessel Transection

In this example, the hemostat devices, as described in Example 3, were tested using a modified model of fatal groin injury in pigs. The model requires partial transection of the femoral arteries in order to prevent vasoconstriction and collapse, ensuring continued severe bleeding. In addition, the time period of free bleeding and the period of application of external pressure were reduced, resulting in higher pressure bleeding at the time of treatment. Thus, the device needed to provide sufficient pressure to remain in contact with the bleeding site. The test protocol/procedure was identical to that described in the Example 3, except for the wound, which entailed a partial transection of the femoral vessels.

Figure 13:
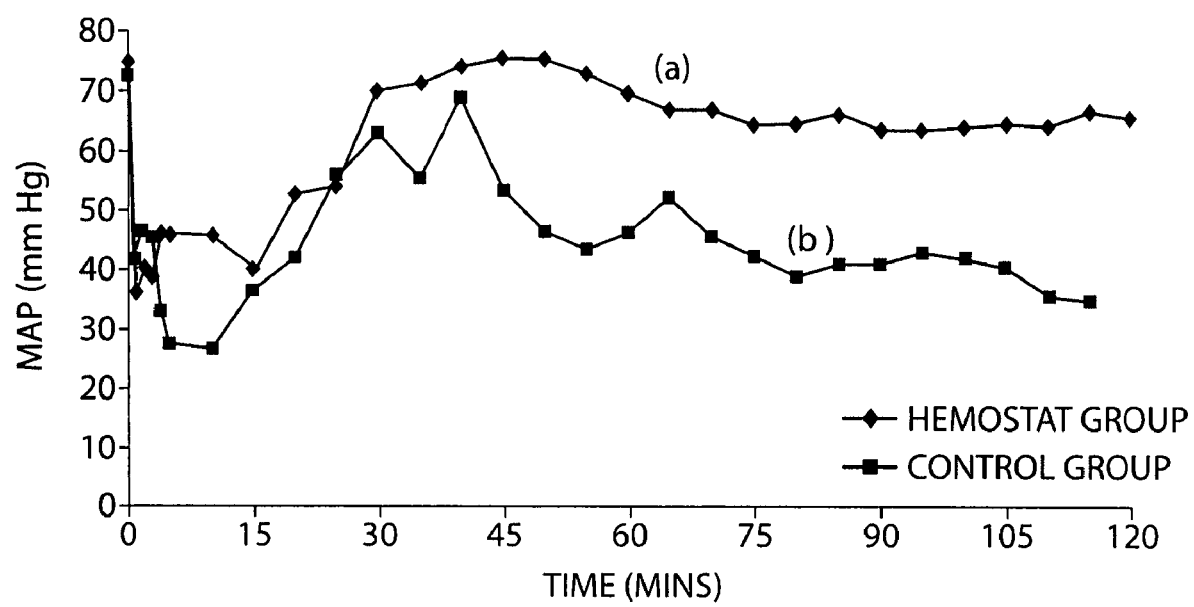
FIG. 13 is a graph showing the average of the mean arterial pressure for (a) the hemostat group and (b) the control group, measured over the duration of the experiments conducted in Example 4.

FIG. 13 shows a graph of the average of the Mean Arterial Pressure for (a) the hemostat group and (b) the control group, measured over the duration of each experiment. The hemostat group showed a significantly higher average MAP, particularly in the early recovery stage before resuscitation and the later stages of resuscitation. This illustrates the efficacy of the swelling hemostatic device in stopping bleeding and holding pressure, which contributed to the overall high survival achieved in testing.

Figure 14:
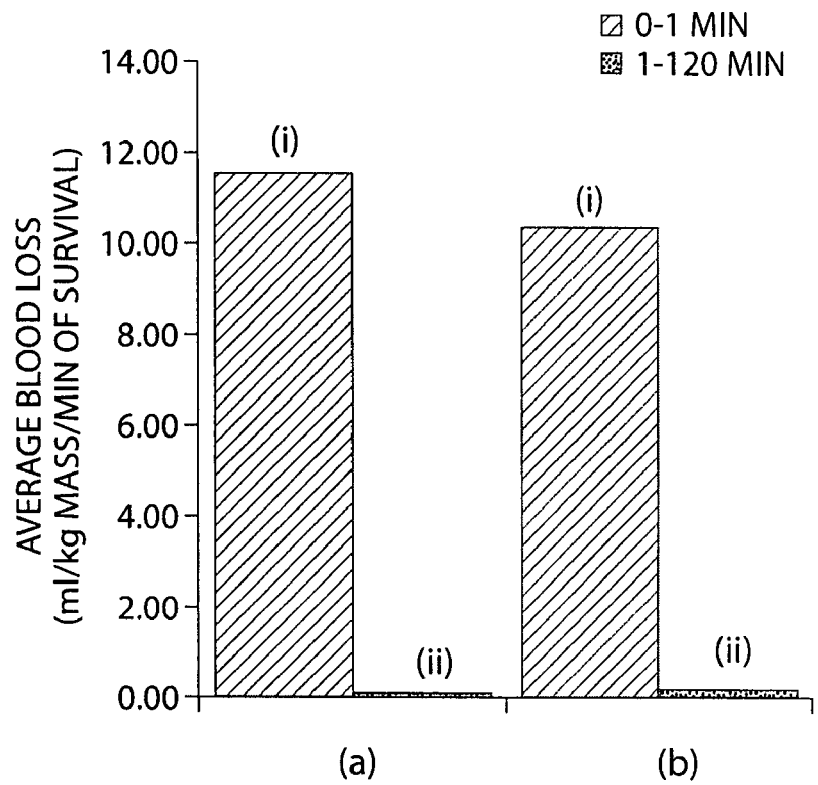
FIG. 14 is a graph describing the (i) pre-treatment and (ii) post-treatment mass and time normalized blood loss for (a) the hemostat group and (b) the control group in Example 5.
Figure 15:
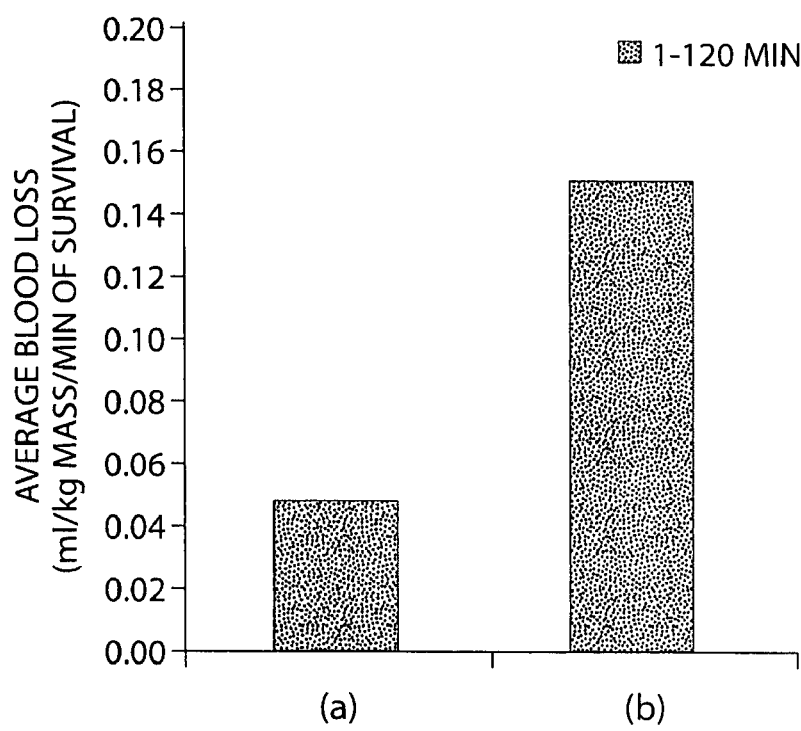
FIG. 15 is a graph describing the post-treatment blood loss for (a) the hemostat group and (b) the control group in Example 4.

FIG. 14 shows a graph describing the (i) pre-treatment (0-1 min) and (ii) post-treatment (1-120 min) mass and time normalized blood loss for (a) the hemostat group and (b) the control group. FIG. 15 shows a graph describing the post-treatment blood loss for (a) the hemostat group and (b) the control group scaled to better show the differences. The pre-treatment rate of blood loss correlated well with the pre-treatment rate of blood loss in Example 3. In addition, the relative reduction in post-treatment blood loss also correlated well with the post-treatment blood loss in Example 3, even though the absolute rate of post treatment blood loss was lower. These results indicate that the swelling hemostatic device was able to effectively control hemorrhage in the partial transection model with reduced application of external pressure.

While several embodiments of the invention have been described and illustrated herein, those of ordinary skill in the art will readily envision a variety of other means and structures for performing the functions and/or obtaining the results or advantages described herein, and each of such variations, modifications and improvements is deemed to be within the scope of the present invention. More generally, those skilled in the art would readily appreciate that all parameters, dimensions, materials, and configurations described herein are meant to be exemplary and that actual parameters, dimensions, materials, and configurations will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto the invention may be practiced otherwise than as specifically described. The present invention is directed to each individual feature, system, material and/or method described herein. In addition, any combination of two or more such features, systems, materials and/or methods, provided that such features, systems, materials and/or methods are not mutually inconsistent, is included within the scope of the present invention.

In the claims (as well as in the specification above), all transitional phrases or phrases of inclusion, such as "comprising," "including," "carrying," "having," "containing," "composed of," "made of," "formed of," "involving" and the like shall be interpreted to be open-ended, i.e., to mean "including but not limited to" and, therefore, encompassing the items listed thereafter and equivalents thereof as well as additional items. Only the transitional phrases or phrases of inclusion "consisting of" and "consisting essentially of" are to be interpreted as closed or semi-closed phrases, respectively. The indefinite articles "a" and "an," as used herein in the specification and in the claims, unless clearly indicated to the contrary, should be understood to mean "at least one."

All references cited herein, including patents and published applications, are incorporated herein by reference. In cases where the present specification and a document incorporated by reference and/or referred to herein include conflicting disclosure, and/or inconsistent use of terminology, and/or the incorporated/referenced documents use or define terms differently than they are used or defined in the present specification, the present specification shall control.

What is claimed is:

1. A hemostatic device for treating a wound, comprising:
porous outer membrane defining a first enclosure having an interior and an exterior; and
a plurality of hemostatic units contained within the interior of the first enclosure,
wherein each hemostatic unit contains a plurality of polymer particles collectively forming a polymeric mass configured to swell in the presence of a fluid, and wherein each hemostatic unit is individually surrounded by and contained within at least one porous inner membrane forming a second enclosure that has an interior containing the plurality of polymer particles.

2. The device of claim 1, wherein each hemostatic unit further comprises means for facilitating transport of fluid into an interior region of the polymeric mass.

3. The device of claim 2, wherein the means for facilitating transport of fluid comprises wicking elements.

4. The device of claim 3, wherein the wicking elements comprise wicking fibers.

5. The device of claim 4, wherein the wicking fibers each have a diameter in the range of 10-150 microns.

6. The device of claim 3, wherein at least a portion of the plurality of polymer particles are bonded to the wicking elements.

7. The device of claim 2, wherein the means for facilitating transport of fluid comprises a hydrophilic material.

8. The device of claim 2, wherein the means for facilitating transport of fluid comprises means for increasing the area for fluid flow within the enclosure.

9. The device of claim 1, wherein the polymer particles are bonded to an inner surface of the inner membrane.

10. The device of claim 9, wherein the polymer particles are bonded to the interior surface of the inner membrane using a surfactant and/or water-soluble adhesive.

11. The device of claim 1, wherein the polymer particles are bonded to a strip of material located in the enclosure.

12. The device of claim 11, wherein the polymer particles are bonded to the strip of material using a surfactant and/or water-soluble adhesive.

13. The device of claim 1, wherein at least one of the porous outer and inner membranes is a microporous membrane.

14. The device of claim 1, wherein the polymer particles comprise polyacrylates.

15. The device of claim 1, wherein the polymer particles comprise sodium polyacrylate.

16. The device of claim 1, wherein the polymer particles comprise poly-anionic beads.

17. The device of claim 1, wherein at least one of the porous outer and inner membranes is formed of an elastic material.

18. The device of claim 1, wherein at least one of the porous outer and inner membranes is formed of nylon, a copolymer of polyurethane and polyethlyene glycol, polyethylene terephthalate, and/or polypropylene.

19. The device of claim 1, wherein at least one of the porous outer and inner membranes comprises pores having an average pore size of 0.15 mm to 1.0 mm.

20. The device of claim 1, wherein at least one of the porous outer and inner membranes comprises pores having an average pore size of 0.2 mm to 0.5 mm.

21. The device of claim 1, wherein the device is sized and configured to be inserted directly into a wound cavity.

22. The device of claim 1, wherein the fluid comprises blood.

23. The device of claim 1, further comprising a bonding agent.

24. A hemostatic device for treating a wound, comprising:
a first porous membrane and a second porous membrane, the first porous membrane and the second porous membrane being sealed together at discrete locations to form a plurality of compartments, each compartment forming an enclosure comprising a hemostatic unit that has an interior and an exterior,
wherein each hemostatic unit contains a plurality of polymer particles within the interior or the compartment, the particles collectively forming a polymeric mass configured to swell in the presence of a fluid.

25. The device of claim 24, wherein each hemostatic unit further comprises means for facilitating transport of fluid into an interior region of the polymeric mass.

26. The device of claim 25, wherein the means for facilitating transport of fluid comprises wicking elements.

27. The device of claim 26, wherein the wicking elements comprise wicking-fibers.

28. The device of claim 27, wherein the wicking fibers each have a diameter in the range of 10-150 microns.

29. The method of claim 25, wherein the means for facilitating transport of fluid comprises means for increasing the area for fluid flow within the enclosure.

30. The method of claim 26, wherein at least a portion of the plurality of polymer particles are bonded to at least a portion of the wicking elements.

31. The device of claim 25, wherein the means for facilitating transport of fluid comprises a hydrophilic material.

32. The device of claim 24, wherein the polymer particles comprise polyacrylates.

33. The device of claim 32, wherein the polymer particles comprise sodium polyacrylate.

34. The device of claim 24, wherein the polymer particles are bonded to an inner surface of at least one of the first and second membrane.

35. The device of claim 34, wherein the polymer particles are bonded to the interior surface of the membrane using a surfactant and/or water-soluble adhesive.

36. The device of claim 24, wherein at least one of the first and second porous membranes is a microporous membrane.

37. The device of claim 24, wherein the polymer particles comprise poly-anionic beads.

38. The device of claim 24, wherein at least one of the first and second porous membranes is formed of an elastic material.

39. The device of claim 24, wherein at least one of the first and second porous membranes is formed of nylon, a copolymer of polyurethane and polyethylene glycol, polyethylene terephthalate, and/or polypropylene.

40. The device of claim 24, wherein at least one of the first and second porous membranes comprises pores having an average pore size of 0.15 mm to 1.0 mm.

41. The device of claim 24, wherein at least one of the first and second porous membranes comprises pores having an average pore size of 0.2 mm to 0.5 mm.

42. The device of claim 24, wherein the device is sized and configured to be inserted directly into a wound cavity.

43. The device of claim 24, wherein the fluid comprises blood.

44. A hemostatic device for treating a wound, comprising:
at least one porous membrane forming at least one enclosure having an interior and an exterior;
a plurality of absorbent polymer particles contained in the interior of the enclosure, the polymer particles collectively forming a polymeric mass and being configured to swell in the presence of a fluid; and
means for facilitating transport of fluid into an interior region of the polymeric mass.

45. The device of claim 44, wherein the means for facilitating transport of fluid comprises wicking elements.

46. The device of claim 45, wherein the wicking elements comprise wicking-fibers.

47. The device of claim 46, wherein the wicking-fibers each have a diameter in the range of 10-150 microns.

48. The device of claim 45, wherein at least a portion of the plurality of absorbent polymer particles are bonded to at least a portion of the plurality of wicking elements.

49. The device of claim 44, wherein the polymer particles are bonded to an interior surface of the porous membrane.

50. The device of claim 49, wherein the polymer particles are bonded to the interior surface of the porous membrane using a surfactant and/or water-soluble adhesive.

51. The device of claim 44, wherein the polymer particles are bonded to a strip of material located in the enclosure.

52. The device of claim 51, wherein the polymer particles are bonded to a strip of material located in the enclosure using a surfactant and/or water-soluble adhesive.

53. The device of claim 44, wherein the at least one porous membrane comprises a first membrane and a second membrane, the first membrane and the second membrane sealed together to form the enclosure.

54. The device of claim 44, wherein the porous membrane is a microporous membrane.

55. The device of claim 44, wherein the polymer particles comprise polyacrylates.

56. The device of claim 44, wherein the polymer particles comprise sodium polyacrylate.

57. The device of claim 44, wherein the polymer particles comprise poly-anionic beads.

58. The device of claim 44, wherein the means for facilitating transport of fluid comprises a hydrophilic material.

59. The device of claim 44, wherein the porous membrane is formed of an elastic material.

60. The device of claim 44, wherein the porous membrane is formed of nylon, a copolymer of polyurethane and polyethlyene glycol, polyethylene terephthalate, and/or polypropylene.

61. The device of claim 44, wherein the porous membrane comprises pores having an average pore size of 0.15 mm to 1.0 mm.

62. The device of claim 44, wherein the porous membrane comprises pores having an average pore size of 0.2 mm to 0.5 mm.

63. The device of claim 44, wherein the device is configured and sized to be inserted directly into a wound cavity.

64. The device of claim 44, wherein the fluid comprises blood.

65. The device of claim 44, further comprising a bonding agent.

66. The device of claim 44, wherein the means for facilitating transport of fluid comprises means for increasing the area for fluid flow within the enclosure.

67. A method of treating a wound, comprising:
inserting a hemostatic device into a wound cavity, wherein the hemostatic device contains a plurality of polymer particles within at least one enclosure formed by one or more porous membranes, the polymer particles collectively forming a polymeric mass configured to swell in the presence of a fluid, the hemostatic device further containing means for facilitating transport of fluid into an interior region of the polymeric mass.

68. The method of claim 67, wherein the means for facilitating transport of fluid comprises wicking elements.

69. The method of claim 68, wherein at least a portion of the plurality of polymer particles are bonded to at least a portion of the wicking elements.

70. The method of claim 67, wherein the device is inserted directly into a wound cavity.

71. The method of claim 67, wherein the device is inserted into a wound cavity together with additional devices.

72. The method of claim 67, wherein the fluid comprises blood.

73. The method of claim 67, wherein the porous membrane comprises pores having an average pore size of 0.15 mm to 1.0 mm.

74. The method of claim 67, wherein the porous membrane comprises pores having an average pore size of 0.2 mm to 0.5 mm.

75. The method of claim 67, wherein the device further comprises a bonding agent.

76. The method of claim 67, wherein the means for facilitating transport of fluid comprises means for increasing the area for fluid flow within the enclosure.

* * * * *